United States Patent
Sakai et al.

(10) Patent No.: US 9,019,498 B2
(45) Date of Patent: Apr. 28, 2015

(54) METHOD FOR INSPECTING DEFECTS, INSPECTED WAFER OR SEMICONDUCTOR DEVICE MANUFACTURED USING THE SAME, METHOD FOR QUALITY CONTROL OF WAFERS OR SEMICONDUCTOR DEVICES AND DEFECT INSPECTING APPARATUS

(75) Inventors: Kazufumi Sakai, Saga (JP); Kazuhiro Nonaka, Saga (JP); Shinsuke Yamaguchi, Kumamoto (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 343 days.

(21) Appl. No.: 13/510,769

(22) PCT Filed: Nov. 19, 2010

(86) PCT No.: PCT/JP2010/070744
§ 371 (c)(1),
(2), (4) Date: Jul. 5, 2012

(87) PCT Pub. No.: WO2011/062279
PCT Pub. Date: May 26, 2011

(65) Prior Publication Data
US 2012/0262715 A1    Oct. 18, 2012

(30) Foreign Application Priority Data

Nov. 20, 2009  (JP) .................................. 2009-264639

(51) Int. Cl.
G01J 4/00      (2006.01)
G01N 21/95    (2006.01)
G01N 21/21    (2006.01)
H01L 21/66    (2006.01)

(52) U.S. Cl.
CPC ............ *G01N 21/9505* (2013.01); *G01N 21/21* (2013.01); *H01L 22/12* (2013.01); *H01L 2924/0002* (2013.01)

(58) Field of Classification Search
CPC ....... G01N 21/956; G01N 21/88; G01N 3/20; G01N 21/219505; G01B 11/30; H01L 22/12
USPC .......... 356/364, 369, 370; 250/559.09; 73/760
See application file for complete search history.

(56) References Cited

U.S. PATENT DOCUMENTS 4,875,170 A * 10/1989  Sakurai et al. .................. 702/34
5,835,220 A * 11/1998  Kazama et al. ............... 356/369

(Continued)

FOREIGN PATENT DOCUMENTS

JP    2008-191120 A      8/2008
JP    2008191120    *   8/2008   ........... G01N 23/225

OTHER PUBLICATIONS

International Search Report for PCT/JP2010/070744 on mailing date Dec. 28, 2010.

*Primary Examiner* — Kara E Geisel
*Assistant Examiner* — Maurice Smith
(74) *Attorney, Agent, or Firm* — Westerman, Hattori, Daniels & Adrian, LLP

(57) ABSTRACT

Light from a light source device is polarized through a polarizer and is caused to impinge obliquely onto an object to be inspected. The resulting scattered light is received by a CCD imaging device having an element for separating scattered polarized light disposed in a dark field. Component light intensities are worked out for an obtained P-polarized component image and an obtained S-polarized component image and a polarization direction is determined as a ratio of them. The component light intensities and the polarization directions are determined from images obtained by imaging of the light scattering entities in a state where static stress is not applied to the object to the inspected and in a state where static load is applied thereto so as to generate tensional stress on the side irradiated by light. The component light intensities and the polarization directions are compared with predetermined threshold values.

20 Claims, 18 Drawing Sheets

(56) References Cited

U.S. PATENT DOCUMENTS

| | | | |
|---|---|---|---|
| 6,349,588 B1 * | 2/2002 | Brown et al. | 73/37 |
| 6,356,347 B1 * | 3/2002 | Watanabe et al. | 356/369 |
| 6,718,269 B2 * | 4/2004 | Sinha | 702/42 |
| 6,797,975 B2 * | 9/2004 | Nishiyama et al. | 250/559.04 |
| 2003/0146263 A1 * | 8/2003 | Farassat | 228/8 |
| 2005/0110988 A1 * | 5/2005 | Nishiyama et al. | 356/237.5 |
| 2009/0130782 A1 * | 5/2009 | Itahashi et al. | 438/6 |

* cited by examiner

Scattered light spot

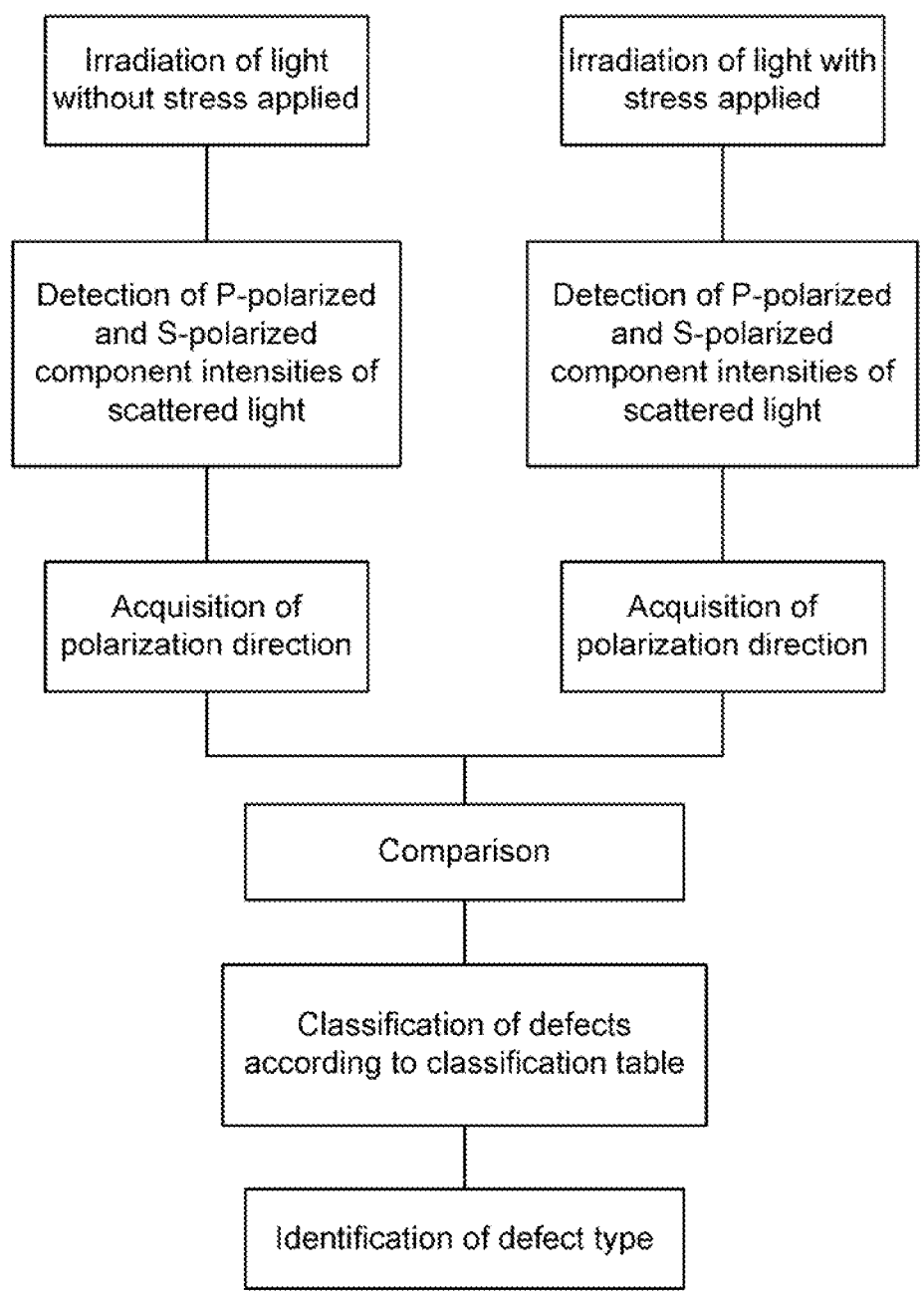

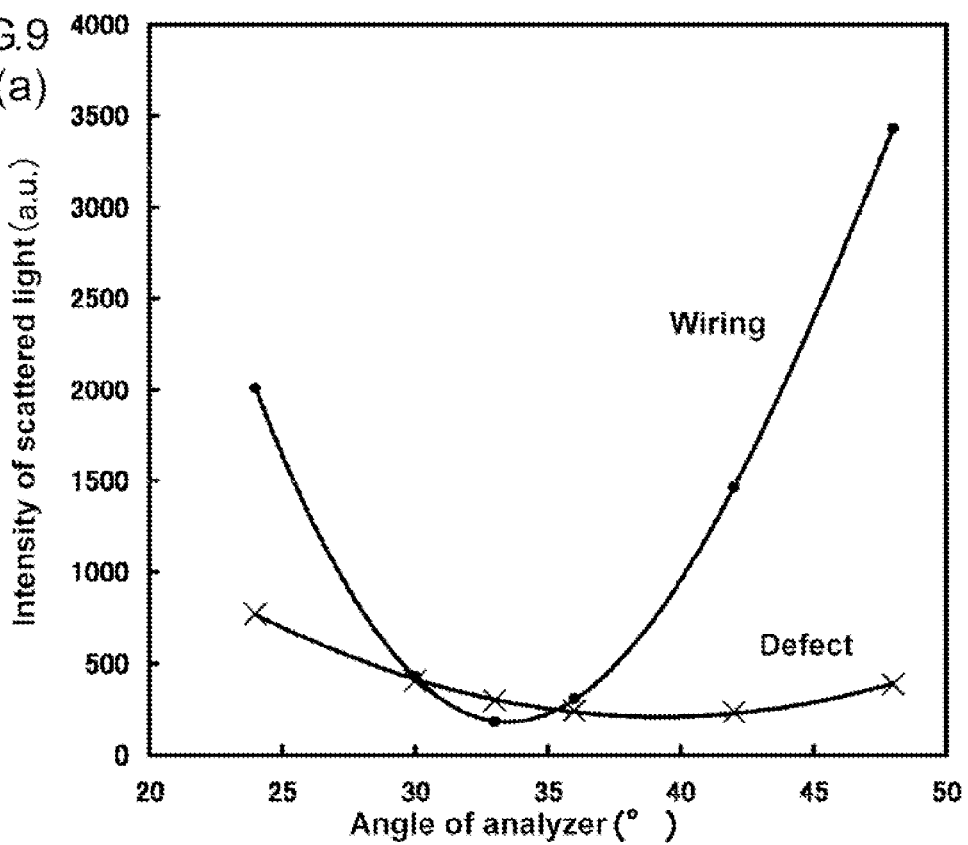
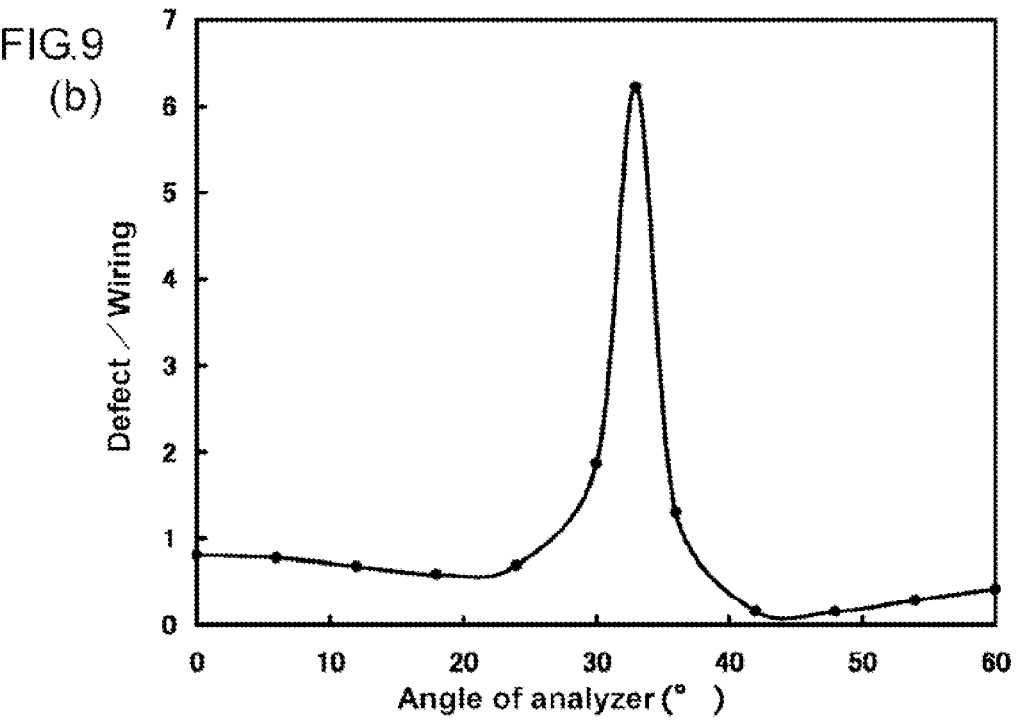

FIG. 11(a) Surface foreign matter
FIG. 11(b) Surface foreign matter
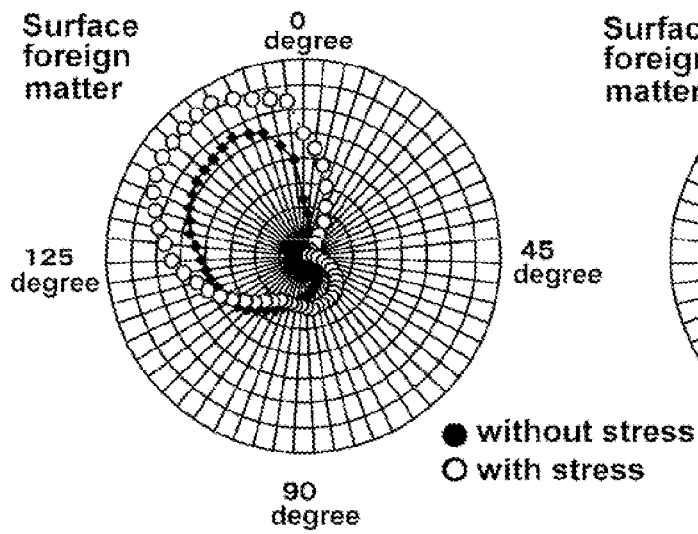
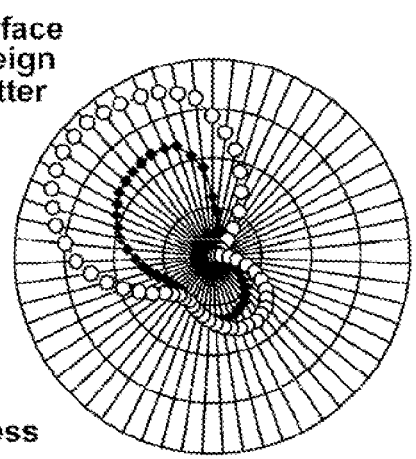
● without stress
○ with stress
FIG. 11(c) Crack
FIG. 11(d) Crack
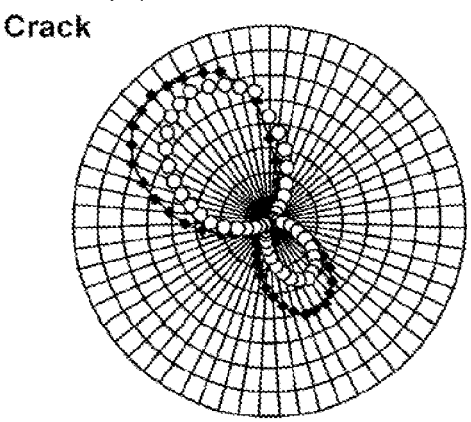
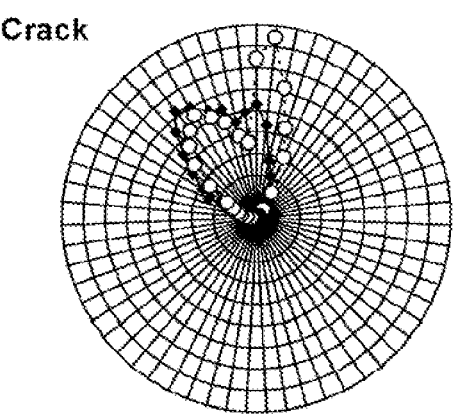
FIG. 11(e) Pattern etc.
FIG. 11(f) Pattern etc.
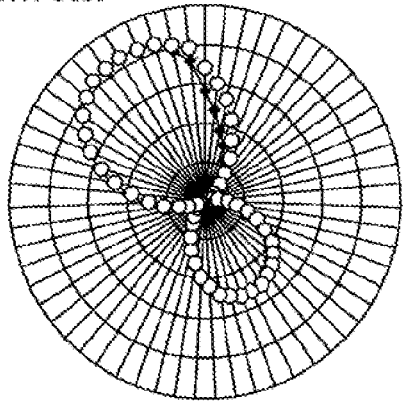
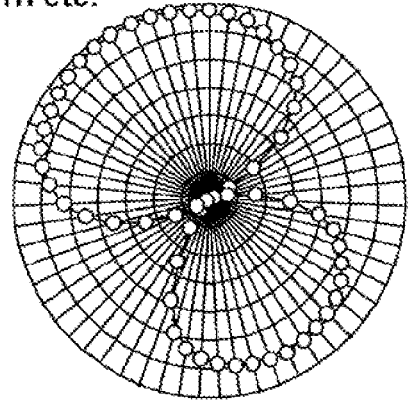

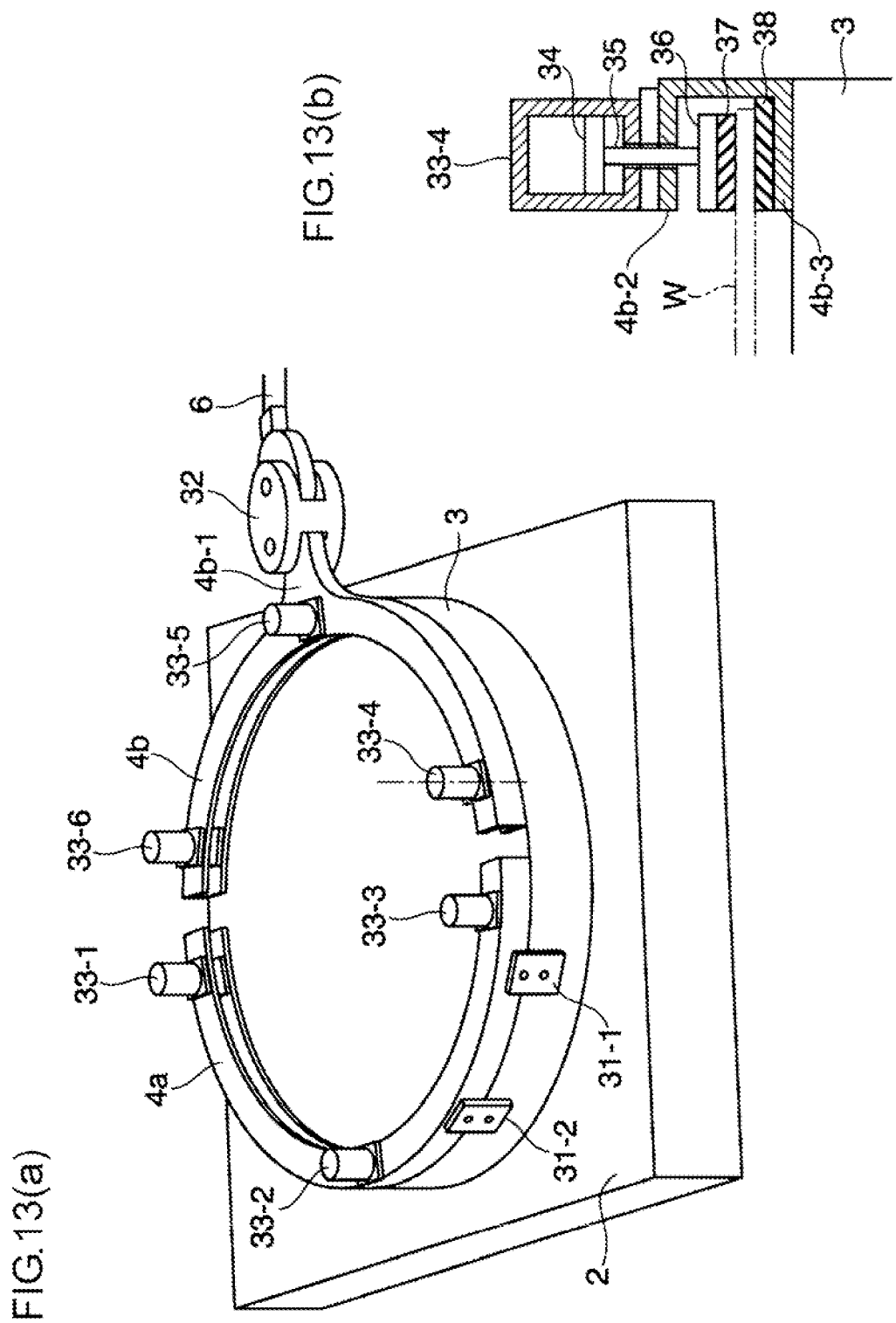

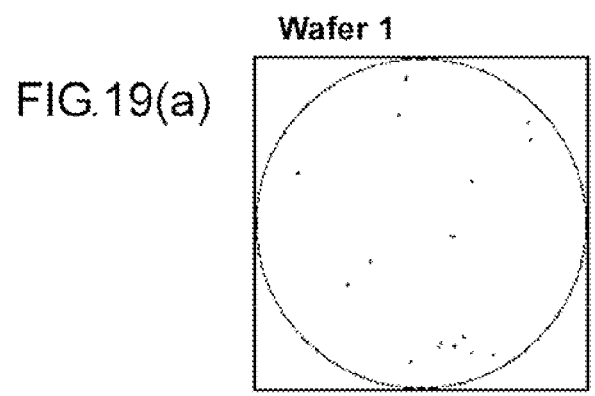
FIG.19(a) Wafer 1
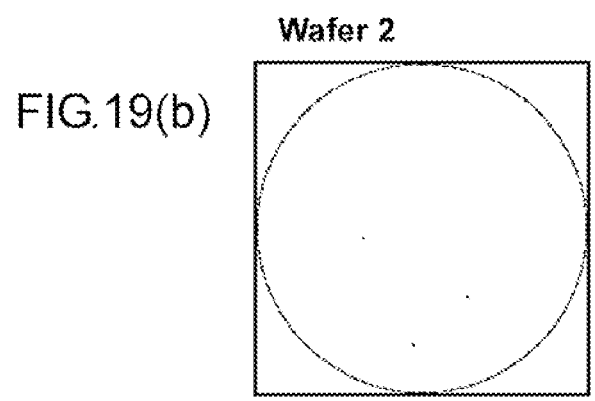
FIG.19(b) Wafer 2
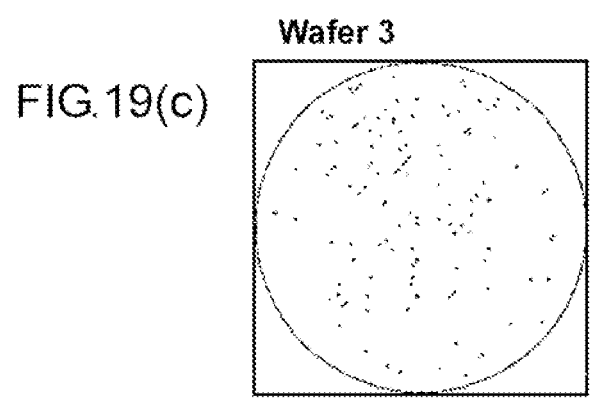
FIG.19(c) Wafer 3
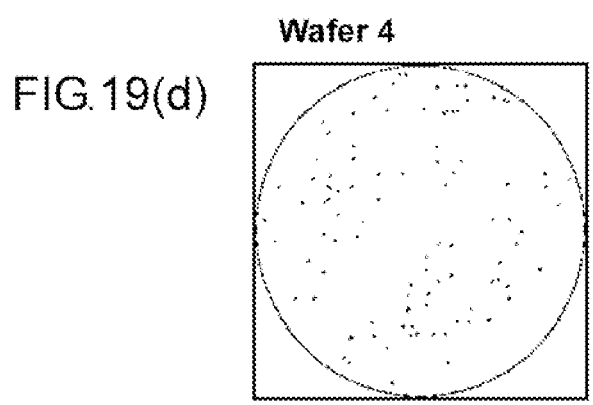
FIG.19(d) Wafer 4

METHOD FOR INSPECTING DEFECTS, INSPECTED WAFER OR SEMICONDUCTOR DEVICE MANUFACTURED USING THE SAME, METHOD FOR QUALITY CONTROL OF WAFERS OR SEMICONDUCTOR DEVICES AND DEFECT INSPECTING APPARATUS

FIELD OF THE INVENTION

The present invention relates to a method for inspecting defects in an object to be inspected, to a wafer for which defect inspection has been performed, to a semiconductor device manufactured using the wafer, to a method for quality control of wafers or semiconductor devices and to a defect inspecting apparatus. Specifically, the present invention relates to a method for inspecting defects through defecting and/or classifying defects in an object to be inspected such as a semiconductor wafer for which high degree of homogeneity and surface smoothness are required, to a wafer for which defect inspection has been performed, to a semiconductor device manufactured using the wafer, to a method for quality control of wafers or semiconductor devices and to a defect inspecting apparatus.

BACKGROUND OF THE INVENTION

In semiconductor manufacturing processes, the presence of defects inside wafers causes deterioration or impairment of electric characteristics in a semiconductor device as a manufactured article. In manufacturing semiconductor devices, therefore, defects in a wafer are inspected at a stage before semiconductor manufacturing or after being subjected to a surface treatment during the manufacturing process.

In the process forming a semiconductor device from a wafer, formation of a thin film, impurity doping or wiring through lithography are made on a wafer, on which an insulator layer is formed. Plurality of wiring layers are formed via insulator layers and flattening is made through chemical-mechanical polishing (CMP) for each insulator layer formation. Humber of wiring layers is 3 to 10 and may over 10 in recent manufacturing processes of system LSI or the like. Insulator layers perform insulation among wirings in a same wiring layer and insulation among wirings in different wiring layers. If wafers with defects are processed for manufacturing, final semiconductor products result in being non-conforming. Therefore, it is necessary to get rid of defects preliminarily in the initial stage of a wafer or a stage where a wiring layer and insulator layer are formed sequentially and flattening is performed.

Recent years have witnessed ever higher degrees of integration in semiconductor devices and ever finer patterns in the devices and thus the size of wafer defects to be inspected has become finer. As an example, electronic machineries have come to be equipped in automobiles as seen in hybrid cars or electric vehicles and more reliability has come to be required for semiconductor devices equipped in automobiles. Defect detection includes destructive methods and non-destructive methods. In the former, the wafer is dissolved in an etching solution or is physically abraded to expose, on the surface, defects that are then observed with a microscope or an electron microscope. However, wafers inspected in accordance with the above methods can no longer be used for semiconductor device manufacturing. Accordingly, in order to realize a device with really high reliability, it is necessary to inspect defects in whole number of articles in-line in a non-destructive method.

Non-destructive inspection methods include electric methods and contactless inspection methods that utilize light or ultrasonic waves. In electric inspection methods, electrodes are attached to the wafer or probes are made to contact with the wafer. Electric signals are then applied to the wafer and the presence of defects in the wafer is detected on the basis of changes in the electric signals. However, it is difficult to point the position of the defects. Also, contact with electrodes or the like is required. Such methods cannot be used thus at the manufacturing stage of articles. Further, it is known that when some electric field is applied during certain time, even though the electric field may be as low as not to create an instant dielectric breakdown, existence of defects may cause metallic constituent of electrodes as Cu or the like to be diffused thereby so that leakage between wirings or electric field breakdown occurs. While this is considered to be one of causes of deterioration due to aging of device products after their shipping, it is difficult to detect such a defect through above mentioned electric inspection.

In defect detection by ultrasonic waves, ultrasonic waves are applied onto the object to be inspected and the ultrasonic waves reflected by defects are detected by a detector. Internal defects in a material through which light cannot pass, such as metals or the like, can be detected and hence the method is used, for instance, for inspecting package interiors. In terms of detection limits and resolving power, however, the method cannot be used for detecting wafer defects and foreign matter with high resolution. In inspection methods that utilize light, light scattered by defects or foreign matter is detected by an optical system placed in dark-field or bright-field and position of defect is detected at the same time. For detecting defects inside wafers, lasers, for which silicon is transparent, are used, while visible-light lasers are used for detecting defects in the surface or surface layers.

Defect inspection schemes that utilize light or ultrasonic waves are disclosed in prior art documents such as the following.

Japan Patent Application Laid-open JP, 562-177447, A (Patent Document 1) discloses an ultrasonic damage inspection method for objects to be inspected such as piping or steel, wherein electromagnetic ultrasonic waves are transmitted to the object to be inspected, a laser beam is aimed at the portion of the object to be inspected that is excited by the ultrasonic waves and defects in the object to be inspected, plate thickness and the like are detected on the basis of resulting reflected signals.

Japan Patent Application Laid-open JP, 2001-208729, A (Patent Document 2) discloses a defect detection device for detecting defects, wherein surface elastic waves from an ultrasonic vibrator impinge on an object to be inspected, a laser beam is irradiated onto the surface of the object to be inspected, the resulting reflected light is received, the frequency difference between the laser output light and the reflected light is detected by a signal processing device and vibration speed in the object to be inspected is measured on the basis of that difference.

Japan Patent Application Laid-open JP, 2005-147813, A (Patent Document 3) discloses a method and device for non-destructive inspection of a material, wherein internal defects of an object to be measured are detected by irradiating a pulsed laser beam onto the surface of the object to be measured, to generate elastic waves thereby; irradiating a continuous-emission laser beam for signals, coaxially with the pulsed laser, onto the surface of the object to be measured; and causing reflected light, influenced by the elastic waves and the scattering surface of the object to be measured, to impinge on a laser interferometer, whereby changes in a frequency component are detected.

Japan Patent Application Laid-open JP, 2002-188999, A (Patent Document 4) discloses that a laser beam is irradiated onto an object to be inspected such as a semiconductor wafer or the like; reflected and scattered light from the object to be inspected is detected in a plurality of directions; and the directionality of the reflected and scattered light is detected through comparison of the detection results, thereby foreign matter and defects, such as flaws or the like, in the object to be inspected being detected as well as distinguished therebetween. Japan Patent Application Laid-open JP, H11-211668, A (Patent Document 5) discloses a defect inspection method wherein a laser beam impinges on a sample to be inspected, the resulting scattered light and the emission light are split into components with a plurality of dissimilar wavelength bands and form images on an imaging device and the nature of the defects is identified on the basis of the obtained plurality of images.

Japan Patent Application Laid-open JP, 2000-216208, A (Patent Document 6) discloses an inspection method in which two pulsed-emission laser beams, set to be at dissimilar incidence angles and have emission timings offset from each other, are irradiated onto the surface of a semiconductor wafer or the like, one of the laser beams being set so as to give rise to scattered light from both particles and pits and the other laser beam being set so that there is less scattered light from pits, wherein particles are distinguished from pits on the basis of the detection results from both types of scattered light.

In the defect inspection methods disclosed in Japan Patent Application Laid-open JP, H10-293101, A (Patent Documents 7) and Japan Patent Application Laid-open JP, H10-293102, A (Patent Document 8), a wavelength $\lambda 1$ at which reflectance R takes a maximum value and a wavelength $\lambda 2$ at which reflectance R takes a minimum value, upon a change of the wavelength of a laser beam that impinges on an object to be inspected, are determined beforehand and optical information at the time at which laser beams of wavelengths $\lambda 1, \lambda 2$ impinge on the object to be inspected, whereby surface defects are distinguished from defects very near the surface layer of the object to be inspected. Also in this, the laser beams impinge obliquely on the object to be inspected and a total image which shows scattering by defects can be observed in a microscope that is disposed above the object to be inspected.

Japan Patent JP, 3664134, B (Patent. Document 9) discloses a method for inspecting a semiconductor wafer surface, wherein a laser beam is irradiated onto and scanned over a wafer surface; light reflected or scattered by the wafer surface is received by a plurality of light-receiving systems having dissimilar light-receiving angles (high angle, low angle) with respect to incident light; and differences between standard reduced particle sizes on the basis of ratios of the light intensities received by the plurality of light-receiving systems are obtained, so as to determine the character and type of the defects.

Japan Patent Application Laid-open JP, 2008-8740, A (Patent Document 10) by the present inventors discloses a method and apparatus in which a laser beam is irradiated onto a wafer surface in a state where ultrasonic waves are being applied onto the wafer and in a state where ultrasonic waves are not applied and the change of intensity of light scattered by cavity defects, from before to after application of ultrasonic waves, is detected by a light-receiving means disposed in a cross-Nicol arrangement with respect to a polarizer, so that foreign matter is determined on the basis of changes in the intensities of the scattered light.

The applicant has proposed techniques disclosed in PCT/JP2009/59460 (Patent Document 11) as one improving the techniques disclosed in Patent Document 10. The techniques consist in irradiating polarized light onto the object to be inspected in a state where no stress is applied to the object to be inspected and in a state where stress is applied to the object to be inspected, separating the scattered light into P-polarized component light and S-polarized component light, obtaining polarization direction and detecting and/or classifying defects by use of intensity of component light and polarization direction. Further, Japan Patent Application Laid-open JP, H04-118540, A (Patent Document 12) and Japan Patent JP, 3,338,118, B (Patent Document 13) disclose methods for detecting defects or the like existing in the object to be inspected by use of change in transmitted light due to distorted field generated around defects (photoelasticity effect).

In Yohei Yamada "Advance of LSI devices and CMP technology supporting it" (Document of No. 145 Committee in the 119 session of "Working of crystal and its assessment" of Nihon gakujutsu shinkokai, pp. 18-23, Oct. 16, 2009: Non-Patent Document 1), description is made concerning requirements and problems in applied process of CMP (chemical-mechanical polishing) technique as an elementary technique inevitable for manufacturing semiconductor devices. Also, it is explained there that cracks may cause short-circuit between wirings and that there is a correlation between defect density and yield of products, that yield changes as inverse of an exponential function of defect density and that defect density over a certain threshold value causes sudden decrease in yield.

In Patent Documents 1 and 2, internal cavity defects cannot be detected with high resolution. In Patent Document 3, the presence or absence of internal defects can be detected but the influence on a scattering surface of the material surface, caused by ultrasonic waves, is detected in the form of signal light. This is appropriate for non-destructive inspection of concrete structures but not for high-resolution inspection of internal defects in semiconductor wafers or the like.

In Patent Documents 4 and 5, the nature of defects is identified on the basis of a relationship between directionalities of reflected or scattered light and wavelength hands. This approach, however, is not appropriate for high-precision detection of internal defects. In Patent Document 6, two pulsed laser beams are irradiated at timings offset from each other, hence the composition and control mechanisms involved are complex. Also, although surface defects such as particles and pits can be detected thereby, the method is not appropriate for detecting internal cavity defects.

In Patent Documents 7 and 8, surface defects and internal defects are distinguished on the basis of wavelength differences. However, it is not possible to determine whether the defects are internal cavity defects or not.

In Patent Document 9, the type and character of wafer surface defects are determined according to a combination of numerical values of standard reduced particle size of scattering elements, on the basis of scattered light intensity ratios at dissimilar light-receiving angles. However, cavity defects inside the wafer cannot be determined thereby.

In Patent Document 10, while defects are inspected by use of application of supersonic waves to the object to be inspected, the stress applied to the object to be inspected is dynamic and it is not easy to control stress and displacement. In the case of an object to be inspected which has a notch or an orientation flat provided for identifying direction, stress distribution according to supersonic waves is affected by the constitution of the object, which affects in turn the result of inspection. Further, the surface is displaced by applied supersonic waves and gives such an effect as changing strength of scattered light, thus giving problems in possibility of detection error and in preciseness of inspection. Along with this, there are problems in complicated apparatus and rather long time required for measurement. Moreover, because detection is performed with S-polarized component alone or P-polarized component alone, there is such a problem that classification of defects can not be done sufficiently.

In Patent Document 10, the scattered light from the object to be inspected is separated into P-polarized component and S-polarized component and kinds of defects can be classified by use of intensities of the polarized components and the polarization direction. However, this technique does not give a sufficiently advantageous method or apparatus in view of actual application of stress to an object to be inspected, specifically in constituting the apparatus for inspecting defects so as to allow stress to be applied securely with means of simple constitution.

In the case where inspection of defects is to be done in light transmission method as disclosed in Patent Document 12 or 13, light can not be transmitted through a wafer with patterns formed and the method of detection by use of light transmitting method can not be used, because multiple layers of metallic wiring patterns are formed on the wafer. Therefore, in detecting foreign matters in a wafer with patterns, it is necessary to employ light scattering method, without employing light transmitting method.

SUMMARY OF THE INVENTION

In inspecting defects in an object to be inspected, such as a semiconductor wafer or the like, cracks or the like in a surface layer could not be detected through conventional electric inspection or through defect inspection using light or stress, as described above. In an object to be inspected such as a semiconductor wafer, the method of removing a defect and the possibility for repair vary depending on the type of the defect. Therefore, it is necessary not only to determine the presence of defects in the object to be inspected but also to determine types of defects. There has been thus a demand for defect inspection that should allow detecting defects with high resolution and classifying the defects with high throughput by distinguishing among defects such as foreign matter on the surface of the object to be inspected, cracks in the surface layer and internal deposits.

In the defect inspection disclosed in Patent Document 10, dynamic stress is applied through deformation of an object to be inspected in a resonance frequency under application of supersonic waves. Considering a case in which supersonic (sonic) waves are applied to a circular object to be inspected such as a wafer, there are plural resonance modes of a circular wafer, one is a mode in which the center of the wafer is a loop of vibration and the other is a mode in which the center of the wafer is a node of vibration. In the mode in which the center of the wafer is a node, stress is not applied in this location. So defect inspection is performed with the mode in which the center of the wafer is a loop.

In this resonance mode, the resonance frequency has tendency to increase in proportion to the wafer thickness, where the resonance frequency of 8 inch wafer with thickness of 730 μm is about 154 Hz. Q value of silicon is so high as to be over $10^4$ and the amplitude of vibration abruptly decreases when vibration is out of resonance. Due to this, in the case where the resonance frequency is 154 Hz, measurement needs be done with frequency step of 154 Hz/$10^4$=0.0154 Hz. In the case where measurement is preformed through a resonance frequency range of 150 to 160 Hz, for which tolerance of wafer thickness is considered, with frequency step of 0.0154 Hz, measurement needs be done for about 650 points. As an enormous number of measurement points are necessitated, time required for measurement becomes long. As its result, throughput in manufacturing process of semiconductor devices is lowered to a large extent, thus making it difficult to apply such measurement to inline inspection in manufacturing process of semiconductor devices for which high throughput is required. Further, equipment for changing frequency, is necessitated in resonance method of supersonic waves so that the defect inspecting apparatus becomes complicated. Moreover, there is such a problem that impedance needs be corrected corresponding to frequencies.

A notch or orientation flat (OF) for indicating face direction is provided on a wafer. On an 8-inch wafer, orientation flat is commonly provided. Existence of an orientation flat causes the resonance frequency of a wafer to change. The resonance frequency of a wafer may change also according to some factor such as: (a) change in wafer thickness during manufacturing process, (b) change in wafer thickness due to wafer tolerance, (c) orientation flat and (d) change in mass due to wiring pattern or the like. These changes affect not only the frequency but also distribution of amplitude. Under such situation, it becomes difficult to control displacement or stress in an object to be inspected using resonance method.

On the other hand, in the case of employing the method in which polarized light is irradiated onto an object to be inspected in a state where no stress is applied to the object to be inspected and in a state where stress is applied to the object to be inspected and the scattered light is detected respectively, it is desired to allow stress to be securely applied on the object to be inspected by use of an apparatus with rather simple constitution. Further, in respect of manufacturing semiconductor devices using wafers, it is desired to make the time required for inspecting step as short as possible.

Further, while flattening is performed through CMP process after a wiring layer and an insulator layer are formed in the manufacturing process of semiconductor devices using wafers, in such process there is a possibility of defects occurring in a wafer depending on conditions due to mechanical elements such as slurry liquid, polishing pads or the like. While such defects can be decreased through making the condition of CPM process optimum, the optimum condition may change as time lapses, so it is necessary to inspect wafers after CPM process.

As described in non-Patent Document 11, defects such as foreign matters, cracks, etc. generated in CMP process of insulator membrane of a wafer may cause pattern defects or short-circuit between wirings in forming wirings and affect quality of manufactured products. Also, it is known that defect density in a wafer over a certain threshold value causes sudden decrease in yield. Considering from these, it has an enormous significance in manufacturing semiconductor devices to confirm through inspection what kinds of defects exist and to what extent the defects amount in a wafer.

Under above mentioned situation, it is an object of the present invention to detect and/or classify defects in an object to be inspected such as a wafer used for manufacturing semiconductor devices with sufficient accuracy and in a short time as well as to detect and/or classify defects at each stage forming a wiring layer, an insulator layer, etc. through CMP process so as to perform quality control of wafers which have been subjected to processing in manufacturing steps of semiconductor devices.

The present invention has been attained, pursuing to solve the above problems. The method for inspecting defects in an object to be inspected according to the invention is a method for inspecting defects in an object to be inspected by polarizing, with a polarizer, light of a wavelength that can penetrate into the object to be inspected and irradiating the polarized light onto a surface of the object to be inspected, thereby detecting scattered light therefrom in a state where static stress is not applied to the object to be inspected and in a state where static stress is applied thereto, said method comprising:

irradiating polarized light obliquely onto the surface of the object to be inspected in a state where static stress is not applied to the object to be inspected and separating scattered light generated as a result of the irradiation into P-polarized component light and S-polarized component light, then obtaining intensity of each component light and polarization direction as a ratio thereof;

irradiating polarized light obliquely onto the surface of the object to be inspected, in a state where static stress is applied to the object to be inspected, at the same position of the surface as when the light was irradiated in a state where no static stress is applied to the object to be inspected and separating scattered light generated as a result of the irradiation into P-polarized component light and S-polarized component light, then obtaining intensity of each component light and polarization direction as a ratio thereof; and detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value; and further characterized in that application of static stress on the object to be inspected is made so as to generate tensional stress on the side of the object to be inspected on which polarized light is irradiated or generate tensional stress in the object to be inspected as a whole.

The method for inspecting defects in an object to be inspected according to the invention, wherein application of static stress to the object to be inspected is made through fixedly holding the object to be inspected at a part on one end in the periphery thereof, grasping the object to be inspected at the part on the other end in the periphery of thereof and pulling it to apply static tensional load to the object to be inspected.

The method for inspecting defects in an object to be inspected according to the invention wherein application of static stress to the object to be inspected is made through holding the object to be inspected at both ends so as to simply supporting the object to be inspected and pressing the object to be inspected at its center position upwards to apply upward static load generating static bending load on the object to be inspected.

The method for inspecting defects in an object to be inspected according to the invention wherein application of static stress to the object to be inspected is made through placing the object to be inspected on a cylindrically shaped bed with plurality of holes connected to a vacuum suction means formed thereon and performing vacuum suction of the object to be inspected by the vacuum suction means to attract the object to be inspected to the surface of the bed thereby causing bending deformation of the object to be inspected.

The method for inspecting defects in an object to be inspected according to the invention, wherein, in respect of light separated with the polarizer into P-polarized and S-polarized components, intensity of scattered light other than by defects is lowered through rotational adjustment of an analyzer which is interposed on the optical axis so as to be adjustable rotationally around the optical axis.

The wafer for which defect inspection has been executed according to the invention is a wafer on which two or more wiring layers have been formed during manufacturing process of semiconductor devices including CMP process and for which inspection has been executed in respect of defects capable of occurrence during CMP process, wherein said defect inspection is performed in a method for inspecting defects in the wafer by polarizing, with a polarizer, light of a wavelength that can penetrate into the wafer and irradiating the polarized light onto a surface of the wafer, thereby detecting scattered light therefrom in a state where static stress is not applied to the wafer and in a state where static stress is applied thereto, said method for inspecting defects comprising:

irradiating polarized light obliquely onto the surface of the wafer in a state where static stress is not applied to the wafer and separating scattered light generated as a result of the irradiation into P-polarized component light and S-polarized component light, then obtaining intensity of each component light and a polarization direction as a ratio thereof;

irradiating polarized light obliquely onto the surface of the wafer, in a state where static stress is applied to the wafer, at the same position of the surface as when the light was irradiated in a state where no static stress is applied to the wafer and separating scattered light generated as a result of the irradiation into P-polarized component light and S-polarized component light, then obtaining intensity of each component light and a polarization direction as a ratio thereof; and detecting defects and/or classifying the defects by comparing the intensity and polarization direction of each component light obtained in a state where no stress is applied to the wafer and the intensity and polarization direction of each component light obtained in a state where stress is applied to the wafer respectively with a predetermined threshold value, said application of static stress to the object to be inspected being made so as to generate tensional stress on the side of the object to be inspected on which polarized light is irradiated or generate tensional stress in the object to be inspected as a whole; and wherein management of defects in the wafer is executed through obtaining the number and/or size of the defects in said method for inspecting defects, collecting data including number of sites exhibiting characteristics of polarized light intensity and polarization direction over a threshold value in the wafer surface, intensity of polarized light and position of polarized light and displaying distribution of defects in the wafer surface and further management of the wafer is executed so that ratio of non-conforming semiconductor devices manufactured from the wafer having potential cause of insufficiency in conduction or in withstand voltage as a result of defects be lower than a management value defined for each semiconductor device.

The semiconductor device according to the invention is a semiconductor device manufactured using the wafer for which defect inspection has been executed.

The wafer for which defect inspection has been executed according to the invention, wherein said wafer is obtained under management of quality control in which the number and/or size of defects capable of occurrence in an insulator layer between upper and lower wiring layers and/or in an insulator layer between wirings in the layer plane are measured.

The semiconductor device according to the invention, wherein said wafer is obtained under management of quality control in which the number and/or size of defects capable of occurrence in an insulator layer between upper and lower wiring layers and/or in an insulator layer between wirings in the layer plane are measured.

The method for quality control of a wafer or a semiconductor device according to the invention is a method for quality control of a wafer or a semiconductor device manufactured using the wafer on which two or more wiring layers have been formed during manufacturing process of semiconductor devices including CMP process and for which inspection has been executed in respect of defects capable of occurrence during CMP process, wherein said defect inspection is performed in a method for inspecting defects in the wafer by polarizing, with a polarizer, light of a wavelength that can penetrate into the wafer and irradiating the polarized light onto a surface of the wafer, thereby detecting scattered light therefrom in a state where static stress is not applied to the wafer and in a state where static stress is applied thereto, said method for inspecting defects comprising:

irradiating polarized light obliquely onto the surface of the wafer in a state where static stress is not applied to the wafer and separating scattered light generated as a result of the irradiation into P-polarized component light and S-polarized component light, then obtaining intensity of each component light and a polarization direction as a ratio thereof;

irradiating polarized light obliquely onto the surface of the wafer, in a state where static stress is applied to the wafer, at the same position of the surface as when the light was irradiated in a state where no static stress is applied to the wafer and separating scattered light generated as a result of the irradiation into P-polarized component light and S-polarized component light, then obtaining intensity of each component light and a polarization direction as a ratio thereof; and detecting defects and/or classifying the defects by comparing the intensity and polarization direction of each component light obtained in a state where no stress is applied to the wafer and the intensity and polarization direction of each component light obtained in a state where stress is applied to the wafer respectively with a predetermined threshold value, said application of static stress on the object to be inspected being made so as to generate tensional stress on the side of the object to be inspected on which polarized light is irradiated or generate tensional stress in the object to be inspected as a whole; and wherein management of defects in the wafer or semiconductor device is executed through obtaining the number and/or size of the defects in said method for inspecting defects, collecting data including number of sites exhibiting characteristics of polarized light intensity and polarization direction over a threshold value in the wafer surface, intensity of polarized light and position of polarized light and displaying distribution of defects in the wafer surface and further management of the wafer is executed so that ratio of non-conforming semiconductor devices manufactured from the wafer having potential cause of insufficiency in conduction or in withstand voltage as a result of defects be lower than a management value defined for each semiconductor device.

The method for quality control of a wafer or a semiconductor device according to the invention is a method for quality control of a wafer or a semiconductor device, wherein management of quality control has been executed for the wafer or semiconductor device so that the number and/or size of defects capable of occurrence in an insulator layer between upper and lower wiring layers and/or in an insulator layer between wirings in the layer plane be measured.

The defect inspecting apparatus according to the invention is a defect inspecting apparatus, comprising:

a support portion on which an object to be inspected is placed;

static stress applying means capable of switching between a state where static stress is applied to the object to be inspected placed on the support portion and a state where no static stress is applied to the object to be inspected;

a light source device that irradiates light with a wavelength that can penetrate into the object to be inspected via a polarizer obliquely onto a surface of the object to be inspected supported by the support portion;

a scanning driving unit that cause the object to be inspected and the light source device to move relatively to each other;

means for separating polarized light disposed at a position in a dark field for receiving scattered light of light irradiated onto the object to be inspected;

light-receiving means having a P-polarized light-receiving section and a S-polarized light-receiving section that separately detect P-polarized component light and S-polarized component light separated by the means for separating polarized light;

a control unit that controls an operation including a static stress application state by the static stress applying means and relative motion of the light source device and the object to be inspected by the scanning driving unit; and a processing unit that detects defects and/or determines types of defects in the object to be inspected by comparing the intensities of P-polarized component light and S-polarized component light as detected by the light-receiving means and a polarization direction thereof obtained as a ratio of the intensities in a state where static stress is applied to the object to be inspected and in a state where no static stress is applied to the object to be inspected respectively with a predetermined threshold value;

wherein said static stress applying means is arranged so as to apply static tensional load to the object to be inspected to generate static tensional stress at least on the surface side of the object to be inspected on which polarized light is irradiated.

The defect inspecting apparatus according to the invention, wherein said support portion of the object to be inspected is equipped with a holding portion on the fixed side holding a part of the periphery of the object to be inspected and a holding portion on the movable side holding another part of the periphery of the object to be inspected, and wherein said static stress applying means applies static tensional load on the object to be inspected by pulling the holding portion on the movable side.

The defect inspecting apparatus according to the invention, wherein said support portion of the object to be inspected is equipped with a pair of holding portions which simply support the object to be inspected at both opposing peripheral ends, and wherein said static stress applying means is equipped with a pressing member for pushing up the object to be inspected at the center position between the opposing ends thereof and static load applying means for applying static bending load to the object to be inspected by pushing up the pressing member to apply upward static load on the object to be inspected.

The defect inspecting apparatus according to the invention, wherein said support portion of the object to be inspected is formed to be a cylindrically shaped bed on which plurality of suction holes are formed so as to communicate with a vacuum suction means via piping and the object to be inspected is deformed by activation of the vacuum suction means so that the object to be inspected be attracted towards the surface of the cylindrically shaped bed and deformed with bending action.

The defect inspecting apparatus according to the invention is a defect inspecting apparatus, wherein a polarizer plate as an analyzer is disposed between the means for separating polarized light and the light-receiving means and the polarizer plate as an analyzer is rotationally adjustable around the optical axis.

In defect inspection of an object to be inspected according to the present invention, a polarized laser beam is irradiated onto the surface of an object to be inspected, P-polarized component light and S-polarized component light of the resulting scattered light are measured simultaneously so that intensities of respective component light and a polarization direction as a ratio thereof are obtained, the intensity of each component light and polarization direction obtained in a state where no stress is applied to the object to be inspected and the intensity of each component light and polarization direction obtained in a state where stress is applied to the object to be inspected are compared respectively with a predetermined threshold value. Based on these, defects in the object to be inspected, such as internal deposits, cavity defects, surface foreign matters, scratches on the surface, or cracks in the surface layer can be detected. Further, kinds of defects can be specified and defects can be classified. Moreover, detection and classification of defects can be performed with sufficient accuracy and in a short time.

In defect inspection using application of supersonic (sonic) waves to an object to be inspected, in which it is not easy to control displacement and stress by use of resonance method and it is necessary to perform measurement for about 650 points in the range of thickness tolerance, thus requiring time for measurement of about 3 hours for inspecting defects. In contrast to this, in defect inspection according to the present invention using application of static stress, measurement is accomplished by measuring two times, that is, whether stress is applied or not. Owing to this, operation in measurement process during defect inspection becomes notably simple. Along with this, time required for measurement can be notably shortened to be several minutes and throughput in manufacturing semiconductor devices is extremely improved. With these, it is realized to perform defect inspection with in-line operation for the first time.

In such a manner, by use of a defect inspecting apparatus according to the present invention for detecting defects, specifying and classifying kinds thereof in an object to be inspected, application of static stress to the object to be inspected can be performed suitably with means of rather simple constitution. Further, inspection of defects can be accurately and efficiently and inspecting process can be accomplished in-inline manner in manufacturing semiconductor devices from wafers.

A method of detecting scattered light from an object to be inspected is employed in defect inspection according to the present invention, so that, even in the case of an object to be inspected which can not be inspected in a method by detecting transmitted light such as a wafer on which metallic wiring patterns are formed in manufacturing steps of semiconductor devices, defect inspection can be performed suitably by placing an analyzer behind the beam displacer and making rotational adjustment around the optical axis so as to remove effects of strong scattered light from metallic wiring patters or the like. Moreover, number and density of defects can be made less than a threshold value and a high yield can be attained with wafers for which the defect inspection according to the present invention has been executed.

Further, the defect inspection according to the present invention makes it possible to perform quality control through inspecting defects in a wafer, on which formation of a wiring layer and an insulator layer and flattening process are accomplished sequentially, collecting data containing number of sites exhibiting properties of polarized light intensity and polarization direction above a threshold value in the wafer surface, polarized light strength and position of polarization and displaying the data as defect distribution in the wafer surface, thus enabling quality control so as to enormously decrease non-conforming products as wafers or semiconductor devices manufactured from them.

BRIEF DESCRIPTION OF THE DRAWINGS

FIG. 8 is a flow chart showing the method for inspecting defects in an object to be inspected according to the present invention;

FIG. 9 is graphs showing results obtained by measuring scattered light with an analyzer disposed behind the beam displacer in FIG. 3, in which (a) shows scattered light intensity with wiring patterns and with defects and (b) shows the ratio of scattered light intensity for defects/wiring patterns;

FIG. 11 is graphs in polar coordinate showing scattered light intensity with an analyzer displaced behind the beam displacer, (a) and (b) for surface foreign matter, (c) and (d) for cracks and (e) and (f) for pattern or the like, respectively;

FIG. 13 (*a*) is a perspective view showing the constitution of a static tensional load applying portion and (b) is a partial sectional view along a plane passing through the line A-A in (a);

FIG. 19 is captured images of defect distribution on wafers subjected to CMP procedure for which defect inspection have been actually performed;

DETAILED DESCRIPTION OF THE PREFERRED EMBODIMENTS

<A> Arrangement of Defect Inspection

In the present invention, a method basically in common with one presented in Patent Document 11 as arrangement of defect inspection is used. So the arrangement of defect inspection according to the present invention containing the common method will be explained at first. In the present invention, defects are inspected through irradiating light onto the surface of an object to be inspected for which it is required to have high homogeneity, the light being of a wavelength capable of penetrating into the object to be inspected and through measuring and analyzing the scattered light of the irradiated light.

Examples of the object to be inspected include wafers for manufacturing semiconductor circuit, such as ICs or the like; substrates for manufacturing optical functional element, such as diffraction gratings; superlattice structures; MENS structures; as well as glass for liquid crystal panels and reticles, etc. High homogeneity is a major issue in all of the foregoing. Aspects of the present invention extend to a method for inspecting defects in an object to be inspected, a wafer subjected to defect inspection or a semiconductor device manufactured using such a wafer, a method for quality control of wafers or semiconductor devices and a defect inspecting apparatus. Considering wafers used for manufacturing semiconductor devices in view of defect inspection, there are wafers as raw material and wafers in the stage in which processing such as wiring has been performed and devices are being formed. After the processing necessary for forming devices has been accomplished, each wafer is separated into individual device through dicing, subjected to bonding and packaging to be formed semiconductor devices.

Figure 1:
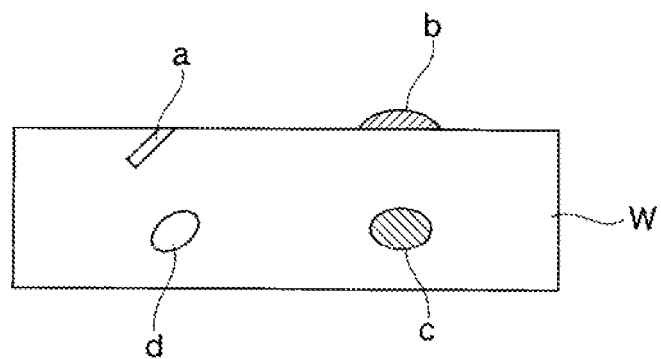
FIG. 1 is a diagram illustrating an example of defects in an object to be inspected.

As illustrated in FIG. 1, defects that impair the functionality of an object to be inspected include, for instance, cracks a in the surface layer, foreign matter (top contamination) or scratches b on the surface, internal deposits c, cavity defects d or the like. The functionality of articles such as semiconductor circuits or optical functional elements manufactured using materials containing such defects can be impaired on account of the defects. Therefore, it is necessary to inspect the products and to determine beforehand whether the defects can be repaired or the article cannot be used.

In the present invention, the light irradiated onto the object to be inspected is of a wavelength capable of penetrating into the object to be inspected. For instance, beam-like light from a laser or obtained through decomposition of light from a halogen lamp is used. A case will be explained here in which a laser is used. The object to be inspected has a high degree of homogeneity, as described above. A silicon wafer for manufacturing semiconductor circuit will be explained here as a typical example.

A laser beam, which is polarized by a polarizer and has a wavelength capable of penetrating into a wafer as an object to be inspected, is irradiated obliquely onto the surface of the wafer and the resulting scattered light is detected by light detection means disposed in a dark field. The above scattered light is detected both in a state where stress is applied to the wafer and in a state where stress is not applied to the wafer. The detection results are analyzed to detect and classify thereby the defects. Here, applied stress is static stress. Other than linearly polarized light, the light polarized by the polarizer may also be elliptically polarized light.

As is known, when cavity defects are present inside the crystal of a wafer, scattered light derived from defects in the crystal preserves the polarization direction of the incident light, in a state where stress is not applied to the wafer. However, the polarization state changes when the object to be inspected is in a stressed state.

As further considered of the dissimilar polarization state of the scattered light depending on whether stress is applied to the wafer or not, the elastic moduli of cavities and silicon are significantly different from each other in internal cavity defects (COP) in the crystal. As a result, application of stress gives rise to elastic strain in the vicinity of the cavities. Internal cavity defects in the crystal are ordinarily octahedral and stress concentrates, in particular, in the vicinity of the corners of the cavities. The strain field in the crystal structure in the vicinity of such local cavities causes the scattered light to contain scattered waves that are polarized in a direction that does not occur in ordinary scattering, i.e. the action of stress in internal cavity defects in the crystal gives rise to a photoelastic effect whereby the polarization state of scattered light varies with respect to that of incident light. As a result, the state of the detected scattered light resulting from internal cavity defects in the crystal is different depending on whether stress is being applied or not.

Cracks on the surface layer of a wafer, or on the insulator film (oxide film) formed on the wafer, exhibit also a photoelastic effect through concentration of stress at the tips of the cracks. As a result, the polarization direction varies depending on whether stress is applied, as in the case of cavities. In contrast to this, in the case of foreign matter on the surface of the object to be inspected, it has been known that the change in the polarization state takes place upon scattering, unlike in the case of internal cavity defects. However, foreign matter on the surface is surrounded by vacuum or gas, hence the photoelastic effect upon application of stress is weak. Thus, the polarization state does not vary particularly depending on whether stress is being applied.

For deposits inside the object to be inspected, it has been checked experimentally whether the polarization direction of scattered light is identical to that of incident light, in the same way as in cavity defects. However, the elastic constant of deposits is ordinarily large, hence stress derived from the strain field is small and the photoelastic effect is weak.

Figure 2:
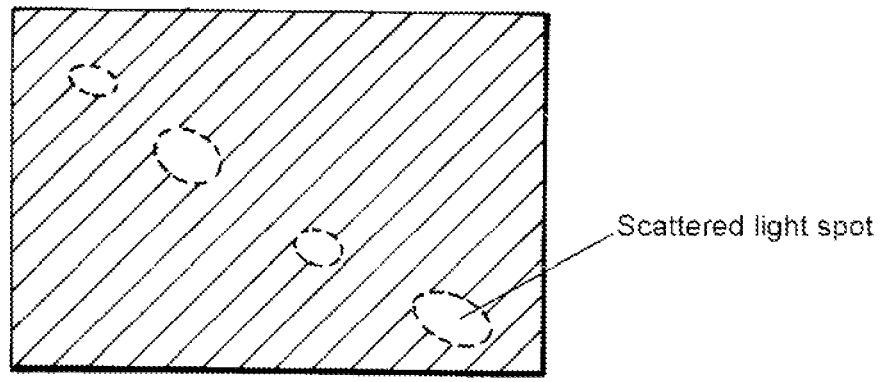
FIG. 2 is a diagram illustrating schematically an example of an image-formation pattern of scattered light caused by defects upon irradiation of a laser beam onto the surface of an object to be inspected.

No scattered light is generated at defect-free sites upon irradiation of a laser beam onto the wafer surface and therefore no scattered light is detected by a two-dimensional light detection means disposed in a dark field. At sites with defects, scattered light is detected by the two-dimensional light detection means. The scattered light is detected in the form of an image wherein bright spots from scattered light are dispersed in a black background, for instance as illustrated in FIG. 2.

In order to concentrate stress in sites of defects under application of stress on an object to be inspected, it is preferable to causes tensional stress to act on the side of the object to be inspected on which polarized light is irradiated. Such tensional stress acts so as to open defects on the surface side of the object for which inspection is to be performed and stress concentration at the leading point of a crack or the like increases. In the case of compression stress, stress concentration does not increase specifically.

Figure 3:
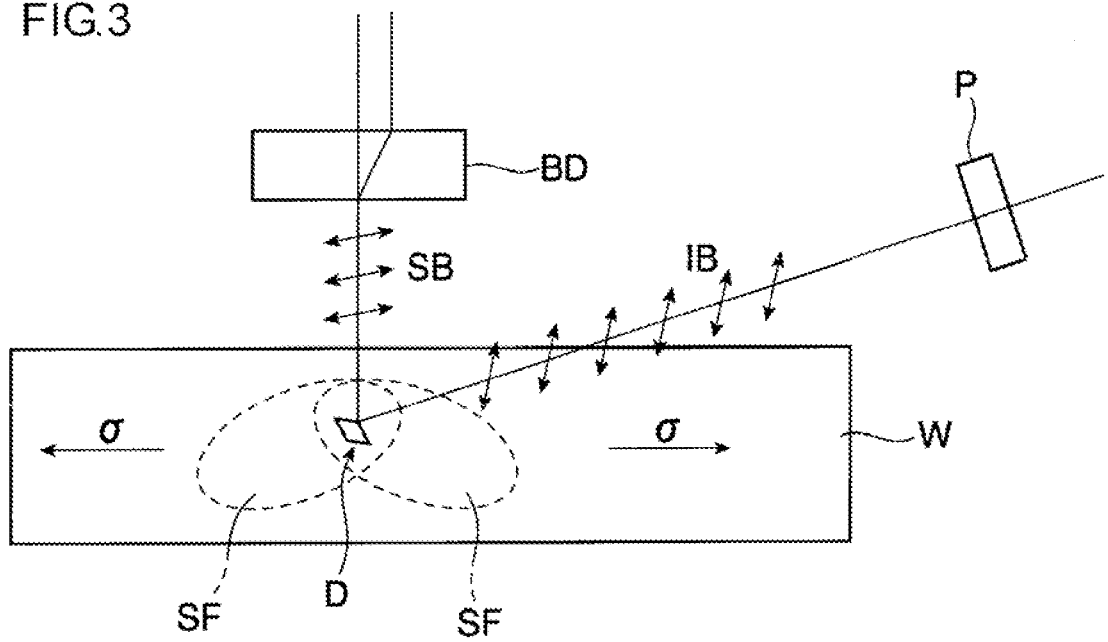
FIG. 3 is a diagram illustrating schematically the principle of inspection of an object to be inspected according to the present invention.

FIG. 3 is a diagram illustrating schematically the principles of inspection of an object to be inspected according to the present invention, wherein defects are detected and classified according to the type of defect. Herein a property is utilized with which a polarized laser beam, having impinged on the object to be inspected W, is scattered by defects so that the features of the scattering as well as changes in the polarization direction vary depending on the type of the defect. A laser beam LB, which has a wavelength capable of penetrating into the object to be inspected W, is polarized by a polarizer P and is obliquely irradiated, as an incident beam IB, onto the surface of a wafer W. A scattered laser beam SB, scattered by a defect D on the surface, in the surface layer or the interior of the wafer W, is separated in respect of polarization by a beam displacer BD disposed in a dark field. Herein, the reference symbol SF denotes the presence of a stress field around a defect in the wafer when the latter is under stress.

Figure 4:
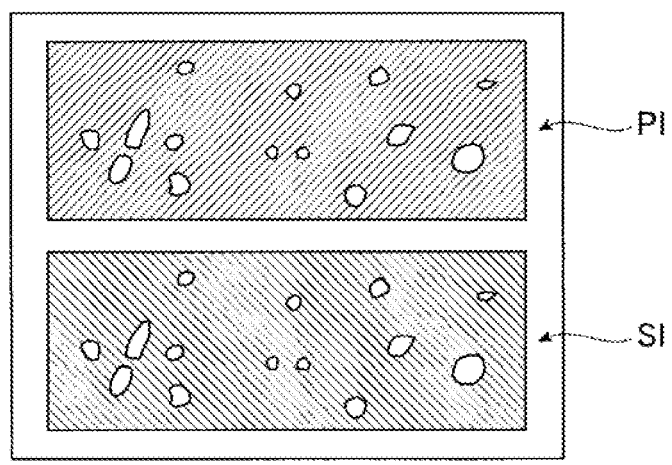
FIG. 4 is a diagram illustrating an example of images formed, on one plane, by dissimilar polarization components of light separated by a beam displacer shown in FIG. 3.

In a case where a calcite beam displacer BD is used, a P-polarized component beam and an S-polarized component beam are separated by about 2 mm (depending on the length of the calcite). When captured by a CCD camera, the beams are imaged in the form of separate images, namely an image (PI) of the P-polarized component light and an image (SI) of the S-polarized component light, as illustrated in FIG. 4. For identical defects, the distribution images (PI, SI) of bright points from scattered light exhibit a similar bright point distribution pattern. However, the characteristics of the respective bright points, such as brightness, are dissimilar between bright points of the P-polarized component light and those of the S-polarized component light. A Wallastone prism may be used as a beam displacer BD.

Here, values are obtained, which characterize the bright points in the image (PI) of the P-polarized component light and in the image (SI) of the S-polarized component light, and then the ratio between the values of both components is worked out. The integrated intensity value of the bright points is obtained, as the above characterizing value, for each image. The integrated intensity value of the bright points results from integrating the brightness values of pixels in an area, which includes the periphery of the bright points, the integration being made for the area. To define the above area, the position of a brightness peak site and the position of an intermediate brightness value, which is the average of the brightness value at the peal; site and a background brightness value, are obtained and then a square, the center of which stands at the peak site position and the sides of which are twice the distance from the peak site to the position of the intermediate brightness value, is taken as the area of brightness integration.

The integrated intensity value of each bright point in the image (PI) is obtained and the data on the position and the integrated intensity value of the bright point are stored. Likewise, the integrated intensity value of each bright point in the image (SI) is obtained and the data of the position and the integrated intensity value of the bright point are stored. The operation of acquiring and storing data of the scattered light intensity (integrated intensity value) at positions, where scattered light is generated upon irradiation of a laser beam onto the wafer surface, and data of the positions, at which bright points are present, is performed in a state where stress is not applied to the wafer and in a state where stress is applied to the wafer.

Next, the polarization directions of scattered light, at the same position of the object to be inspected, in a state where no stress is applied and in a state where stress is applied are compared to work out a polarization direction difference and it is determined whether that difference exceeds a threshold value or not. This constitutes a benchmark for defect type determination. Elliptically polarized light may also be used as the polarized light in the present invention, besides linearly polarized light. In the case of elliptically polarized light, the long axis direction thereof is the polarization direction.

Figure 5:
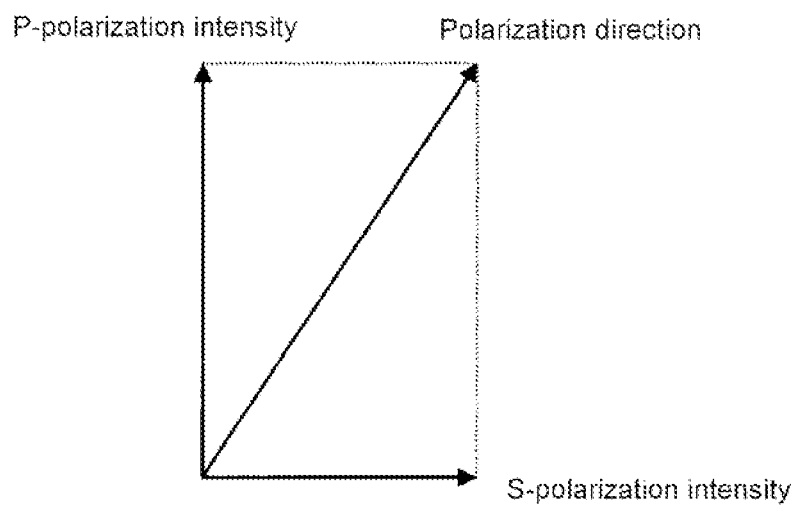
FIG. 5 is a diagram illustrating a relationship between component light intensities and polarization direction.

The polarization direction of scattered light is obtained on the basis of the polarized light intensity represented by the integrated intensity values obtained for each bright point, as illustrated in FIG. 5. In FIG. 5, the P-polarization intensity is the polarized light intensity for a bright point of those in the image (PI) and the S-polarization intensity is the polarized light intensity for a bright point corresponding to the image (SI). The ratio between P-polarization intensity and S-polarization intensity, which corresponds to a tangent function, represents the polarization direction. The polarization direction is thus defined to be a magnitude obtained as the ratio between P-polarization intensity and S-polarization intensity. The polarization direction is obtained also for the incident light.

Figure 6A:
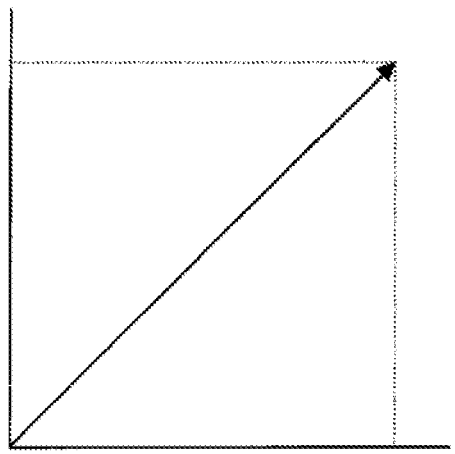
FIG. 6(*a*) is a diagram illustrating an example of polarization direction of incident light and FIG. 6(*b*) is a diagram illustrating an example of polarization direction of light scattered by defects.
Figure 6B:
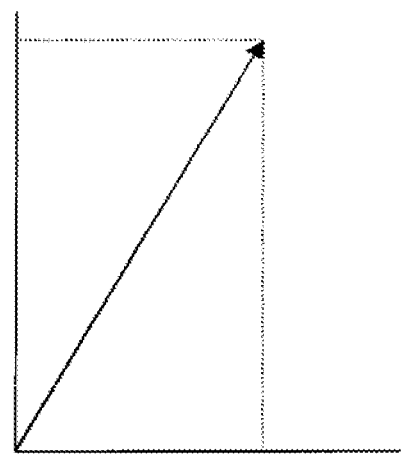

FIG. 6(a) illustrates an example of the polarization direction of incident light and FIG. 6(b) illustrates an example of the polarization direction of such scattered light that incident light having the polarization direction of FIG. 6(a) has been scattered by defects in the wafer. The polarization direction of the scattered light varies depending on the scattering entities (defects) and ordinarily deviates somewhat from the polarization direction of incident light.

Figure 7A:
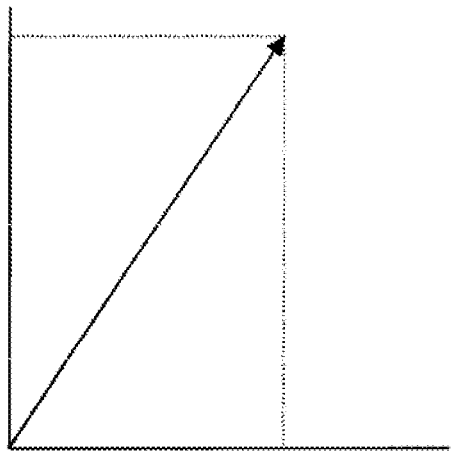
FIG. 7 is a diagram illustrating an example of polarization direction during application of stress to an object to be inspected, in which FIG. 7(*a*) illustrates an instance where defects are absent and FIG. 7(*b*) illustrates an instance where defects are present.
Figure 7B:
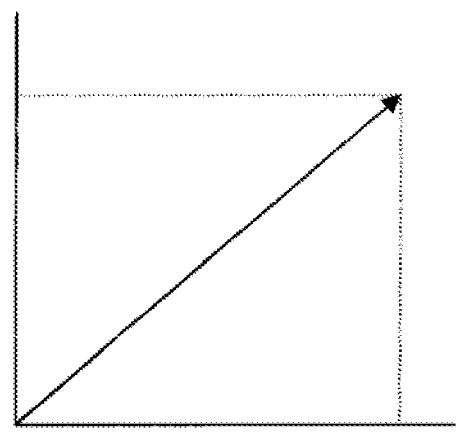

FIGS. 7(a), 7(b) illustrate comparatively an instance where cracks and/or cavity defects are absent and an instance where the foregoing are present respectively. FIG. 7(a) illustrates an instance where no cracks or cavity defects are present and the polarization direction does not change upon application of stress. In a case where cracks and/or cavity defects are present, the polarization direction changes through application of stress, as illustrated in FIG. 7(b). Here, in FIGS. 6 and 7, the ordinate and the abscissa denote P-polarization intensity and S-polarization intensity, respectively, similarly as in FIG. 5.

When the difference in the polarization directions of scattered light between a state in which stress is applied and a state where no stress is applied is large enough to exceed a given threshold value, the scattered light is deemed to arise from cracks or from internal cavity defects in the crystal; when the difference in the polarization directions of scattered light between a state in which stress is applied and a state where no stress is applied is smaller than a given threshold value and does not vary much, the scattered light is deemed to arise from surface foreign matter or from deposits. In such a manner, defects are classified on the basis of detection results of the scattered light. The threshold values, which vary depending on the type of object to be inspected, such as a wafer, and on the nature of the defects, are to be obtained beforehand in accordance with, for instance, the types of the objects to be inspected.

Types of defects can be classified according to the presence or absence of changes in the polarization direction and to the intensity of polarized light. Classification is summarized in such a form as Table 1.

TABLE 1

| Defect types | Without stress application | | With stress application | | Polarization direction |
|---|---|---|---|---|---|
| | S-polarized light | P-polarized light | S-polarized light | P-polarized light | |
| Internal deposits | Strong | Very weak | Small change | Small change | x at or below threshold value |
| Cavity defects | Strong | Very weak | Change | Change | o at or above threshold value |
| Surface foreign matter | strong | strong | Small change | Small change | x at or below threshold value |
| Cracks | Weak | Very weak | Change | Change | o at or above threshold value |

In Table 1, the polarization direction of incident light is S-polarization. That is because an S-polarized component is ordinarily used for observing internal defects. The changes in the polarization direction due to the various defects are explained next.

Internal Deposits

It is confirmed experimentally that the polarization direction of incident light is conserved in scattered light for internal deposits. In the absence of applied stress, the light is scattered as-is and the polarization direction does not change. The scattered light intensity changes upon generation of a stress field around internal deposits through application of stress. However, the effect is small and the change in the polarization direction is no greater than a threshold value.

Cavity Defects

Similarly to internal deposits, the polarization direction of scattered light is conserved in the case of internal cavity defects. Accordingly, in the absence of applied stress, scattered light behaves in the same way as in the case of internal deposits. Both the P-polarized component and the S-polarized component change upon generation of a stress field around cavity defects through application of stress. The polarization direction changes also as a result.

Surface Foreign Matter or Scratches

Surface foreign matter does not preserve the polarization direction, due to depolarization effects. Therefore, a strong S-polarized component is observed even upon incidence of P-polarized light. If the polarization direction of incident light and the polarization direction of scattered light are significantly dissimilar in the absence of applied stress, it is determined at that point in time that the defect is surface foreign matter. (Even under applied stress, only a very weak stress field is ordinarily present around surface foreign matter, hence the polarization direction does not change.)

Cracks

Cracks are defects that reach from the surface to the interior and can be thought of similarly as cavity defects. The radius of curvature at the tip of the crack is extremely small. Therefore, greater stress than in the case of cavity defects concentrates at the tips of cracks and the change in polarization direction is greater than that in cavity defects.

Penetration depth of light irradiated on an object to be inspected is variable depending on its wave length, so kinds or wave length of irradiated light are selected corresponding to the condition as to substance of the object to be inspected or to what depth observation is to be performed. In the case of a bare wafer for manufacturing semiconductor devices, penetration depth of visible light laser is several microns from the surface. In contrast to this, penetration depth of infrared light laser reach the whole content of the wafer, thus being adapted to detection of cavity defects within the wafer. On the other hand, visible light allows cracks or cavity defects within the oxide film formed on a wafer to be detected, because such oxide film is transparent for visible light.

The process of detecting defects in an object to be inspected is such as shown in the flow chart of FIG. 8.

Because a wafer before manufacturing process of semiconductor devices is homogeneous as a whole, defects in such a wafer can be classified with an inspecting apparatus which is arranged to separate scattered light beam (SB) from the object to be inspected into polarized components and perform detection. In the case of a wafer which is in manufacturing process, patterns of metallic wirings or the like are formed on its surface. In performing detection and classification of defects as mentioned above, intense scattering of laser incident on the wafer occurs and such intense scattered light is detected along with light scattered by defects, giving influence on detection and classification of defects.

In such a manner, in order to perform detection and classification of defects accurately in the case of a wafer on which patterns of metallic wirings or the like are formed, it is necessary to decrease intensity of light scattered by such metallic patterns or the like. Referring to a schematic diagram of defect inspection shown in FIG. 3, laser polarized with a polarizer P, incident on a wafer W and scattered thereby is transmitted through a beam displacer BD and then through an analyzer. After this, intensity of the scattered light is measured, giving a result as shown in FIG. 9(*a*). The abscissa denotes angular position of the analyzer.

Figure 10:
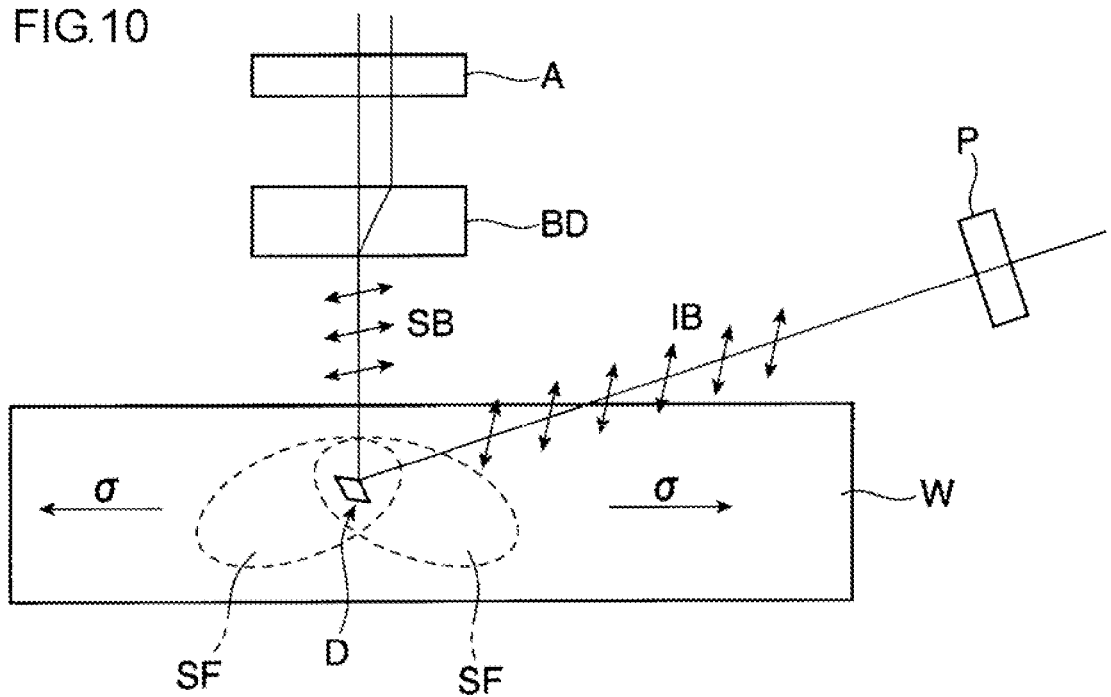
FIG. 10 is a diagram illustrating the arrangement of measurement in which an analyzer is disposed behind the beam displacer in FIG. 3.

As shown in FIG. 9(*a*), while light scattered by wiring patterns is especially weak at about 33 degrees and intense in other range, light scattered by defects does not vary so much. Ratio of scattered light intensity by defects to scattered light intensity by wiring patterns corresponding to angle of the analyzer (defects/wirings) is as shown in FIG. 9(*b*) and the ratio is especially high at about 33 degrees. From this, by disposing an analyzer (a polarizing plate as an analyzer) A behind the beam displacer BD as shown in FIG. 10 and rotationally adjusting it around the optical axis, it is possible to decrease the intensity of light scattered by the wiring patterns compared to the intensity of light scattered by defects, thereby extremely decreasing the influence of the wiring patterns on detection and classification of defects. FIG. 10 shows an arrangement similar to that shown in FIG. 3 expect the analyzer A being dispose behind the displacer BD.

Polarized component is kept in intense light scattered by wiring patterns. Scattered light is substantially of S-polarized component when incident light is S-polarized and does not contain basically P-polarized component. Scattered light is substantially of P-polarized component when incident light is P-polarized. When light incident on the object to be inspected is of S-polarized, angular adjustment of the analyzer is made so as to be substantially parallel to the P-polarized direction, the angle being such that S-polarized component can be scarcely transmitted. With this, while intensity of intense light scattered by wiring patterns substantially of S-polarized component is greatly decreased, intensity decrease of P-polarized component is small in extent compared to intensity decrease of S-polarized component.

In such a manner, by causing the light polarized and separated through the beam displacer to be transmitted through the analyzer, almost all of intense light scattered by wiring patterns is cut off so that its signal level can be lowered. Then, S-polarized component is adjusted to be a signal level comparable with P-polarized component. To say in view of improving robustness of measurement, ratio of polarized light components P/S has importance and it is essential not to cut off all of S-polarized light component. "To be substantially parallel to the P-polarized direction" in relation to angular adjustment of the above mentioned analyzer corresponds to this. Further, when an analyzer is disposed behind the beam displacer, whole signal intensity is lowered by the amount. However, this amount is not so great as to cause a problem in actual defect inspection.

FIG. 11 shows graphs in polar coordinate showing scattered light intensity obtained for each rotational angle in cases where the beam displaces (BD) is replaced with a polarizer element and the polarizer element is rotated (0-180 degrees). In the graphs, (a) and (b) are for surface foreign matter, (c) and (d) are for cracks and (e) and (f) are for pattern or the like, respectively. Solid line (•) denotes the case where static stress is not applied and dotted line (○) denotes the case where static stress is applied. P-polarized light component is intense for surface foreign matter, so the intensity is not zero near 110 degrees (the angle varies according to analyzer angle). That is, P-polarized light component appears near 110 degrees. In the case where cracks exist, intensity ratio of P-polarized light component and S-polarized light component varies. Due to this, the angle corresponding to the maximum intensity varies (it seems to be rotated in the graph) and cracks are clearly distinguished from surface foreign matter or patterns. Further, for patterns, similar situation of polarization results irrespective as to whether stress is applied or not. In such a manner, by examining polarized light component in detail, surface foreign latter, cracks and patterns can be separated more clearly.

As mentioned above, as for static stress applied on the object to be inspected such as a wafer, it is effective in view of accuracy and efficiency in defect inspection to cause tensional stress to act on the side of the object to be inspected on which polarized light is irradiated so that such tensional stress acts so as to open defects on the surface side of the object for which inspection is to be performed. It will be explained below in relation to a defect inspecting apparatus as to how such static tensional stress is actually applied on an object to be inspected such as a wafer.

<B> Defect Detection Apparatus

One embodiment of the defect inspecting apparatus for inspecting an object to be inspected according to the present invention will be explained with reference to FIG. 12. The explanation will focus on an instance where the object to be inspected is a silicon wafer for manufacturing semiconductor circuits and laser light is used as the irradiation light.

Figure 12:
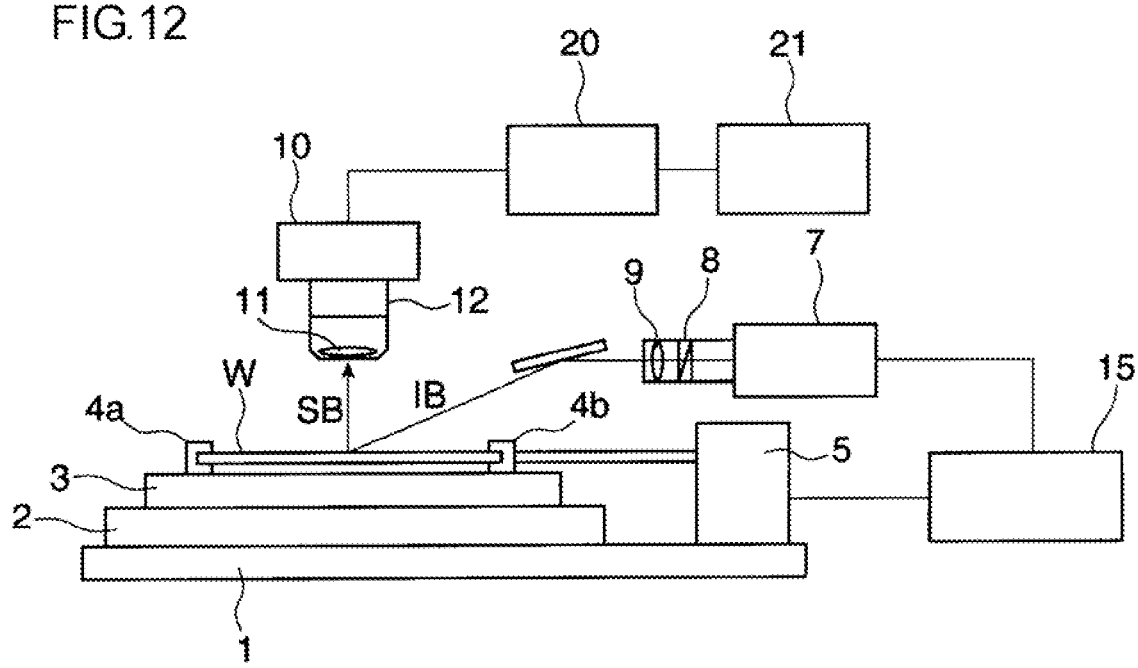
FIG. 12 is a view schematically showing a defect inspecting apparatus of a type applying static tensional stress according to the present invention.

FIG. 12 shows schematically the constitution of a defect inspecting apparatus in a configuration in which stress on a wafer as an object to be inspected is applied through applying tensional load. Here, the reference numeral 1 denotes a base and the reference numeral 2 denotes a X-Y stage which is mounted on the base 1 and driven in X and Y directions and which includes a movable element in X-direction and a movable element in Y-direction. The reference numeral 3 denotes a wafer supporting bed fixed to the upper movable elements of the X-Y stage 2 and a wafer holding portion on the fixed side 4a is fixed on the wafer supporting bed 3, while a wafer holding portion on the movable side 4b is placed on the wafer supporting bed 3. The reference numeral 5 denotes a tensional load applying portion, which pulls the wafer holding portion on the movable side 4b via a pulling rod 6 connecting the tensional load applying portion 5 and the wafer holding portion 4b and applies tensional load on a wafer held by the wafer holding portions 4a, 4b. The part of the wafer holding portions 4a, 4b are shown here in section.

The reference numeral 7 denotes a laser device, for which a laser, for example, with frequency of 375 nm is employed and which is provided so as to irradiate laser light obliquely on the surface of a wafer W. The reference numeral 8 denotes polarizer for imparting polarization to laser light, the reference numeral 9 denotes a condenser lens and the reference character M denotes a mirror. The reference numeral 10 denotes a CCD imaging device disposed at the dark field position for receiving the scattered light beam SB from the incident light beam IB to which polarization is imparted by the polarizer 8 and which is incident on the surface of the wafer W. The reference numeral 11 denotes the objective lens. The reference numeral 12 denotes a beam displacer which separates the light transmitted through the objective lens 11 into respective polarization components.

In the case where an analyzer for decreasing the influence of light scattered by wiring patterns or the like is provided, polarizing plate as an analyzer is disposed behind the beam displacer so as to be rotatable around the optical axis. It is preferable to incorporate elements such as objective lens 11, beam displacer 12, analyzer, etc. into a mounting drum in an assembled manner and to attach the mounting drum to the body of a CCD imaging device. In this, analyzer is preferably made rotatable through external manipulation with a ring or the like.

The reference numeral 15 denotes a driving control unit, which performs displacement control of the wafer W in the X-Y direction by way of the X-Y stage 2, control of load application on the wafer W by way of the load applying portion 5 and control of operation of the laser device. The reference numeral 20 denotes an image analyzing/processing device for carrying out computing process of image data from scattered light, as captured by the CCD imaging device, with storage means necessary for image analysis and processing provided. The reference numeral 21 denotes a display for displaying, for example, images obtained by the CCD imaging device, as well as results of the analysis and processing.

FIG. 13(a) shows the parts of the wafer holding portion and the tensional load applying portion in more detail in a perspective view, in which the wafer is not shown. In FIG. 13(a), the reference numeral 2 denotes an upper movable portion of the X-Y stage (or an integral portion thereof), the reference numeral 3 denotes a wafer supporting bed fixed to the upper movable elements of the X-Y stage 2, the supporting bed having a configuration of circular bed to be adapted to the shape of a wafer W. On the upper side of the wafer supporting bed 3, a wafer holding portion on the fixed side 4a with a substantially semicircular shape is fixed on the wafer supporting bed 3 so as to swing about the center point and a wafer holding portion on the movable side 4b with a substantially semicircular shape is placed on the wafer supporting bed 3. The wafer holding portions on the fixed side and on the movable side 4a, 4b are of a substantially semicircular shape respectively and combination of them forms a substantially circular shape. Each of the wafer holding portions has a groove with a shape in section like a character ⊃ (U) and is a member for holding the peripheral edge portion of the wafer in this groove via elastic member such as rubber.

The wafer holding portion on the fixed side 4a has a pin 31 (not shown) protruding downwards under its center position and the pin 31 is inserted into a hole formed correspondingly on the wafer holding bed 3. In such supporting arrangement by use of a pin, the wafer holding portion 4a is supported on the wafer supporting bed 3 so as to swing in its plane. The pin 31 has sufficient strength to bear the tensional load applied on the wafer.

The wafer holding portion on the movable side 4b has a protruded portion 4b-1 at its center position, which is connected to the pulling rod 6 via a connecting portion 32. On the upper side of the wafer holding portion 4a, 4b, air pressure cylinders 33-1, 33-2, . . . and 33-6 are provided. At these sites through-holes are formed on the upper side of the wafer holding portions 4a, 4b respectively, through which connecting rods of the air pressure cylinders 33-1, 33-2, and 33-6 pass and can make pushing action on the periphery of the wafer respectively. Compressed air is supplied to each of these air cylinders via air supplying pipes (not shown).

FIG. 13(b) shows the part concerning to the air pressure cylinder 33-4 among the air pressure cylinders shown in FIG. 13(a). In this view, the part is shown in a section in the plane extending through center axial line A-A and the center of the wafer supporting bed 3 and the wafer W is shown with imaginary line. The wafer holding portion on the movable side 4b is placed on the wafer supporting bed 3 and the air pressure cylinder 33-4 is secured to the upper side of the wafer holding portion 4b. The connecting rod 35 integrally secured to the piston 34 reciprocated within the cylinder 33-4 extends through the hole formed in the upper plate 4b-2 of the wafer holding portion 4b. A flange 36 is secured to the forward end of the piston 35.

A cushion member 37 made of rubber is caused to adhere to the underside face of the flange 36. Also, a cushion member 38 made of rubber is caused to adhere to the upper side face of the lower plate 4b-3 of the wafer holding portion 4b. When the air pressure cylinder 33-4 is activated to urge the piston 34 downwards, the periphery of the wafer W is grasped between the cushion members 37 and 38 so that surfaces of the wafer may not suffer from damage. The other air pressure cylinders have a similar constitution.

When defect inspection is to be performed with stress applied on the wafer by use of the defect inspecting apparatus with the wafer holding portion and the tensional load applying portion as shown in FIG. 13(a),(b), each of the air pressure cylinders 33-1, 33-2, . . . and 33-6 are kept in deactivated situation and the wafer supporting portion on the movable side 4b is kept to be in retracted position at first. In this situation, a wafer W is brought into such position that its periphery is inserted between the cushion members 37 and 38 corresponding to the respective air pressure cylinders 33-1, 33-2 and 33-3 provided on the wafer holding portion on the fixed side.

After this, the wafer holding portion on the movable side 4b is caused to advance so that the periphery of the wafer comes in between the cushion members 37 and 38 corresponding to the respective air pressure cylinders 33-4, 33-5 and 33-6 provided on the wafer holding portion on the movable side 4b. With this, the situation is set up that the wafer is placed between the wafer holding portions 4a and 4b shown in FIG. 13(a). From this situation, by supplying pressurized air to each of the air pressure cylinders 33-1, 33-2, . . . and 33-6 and pressing the periphery of the wafer to be held between the cushion members 37 and 38 with air pressure, situation for defect inspection with no stress applied on the wafer W is set up.

In order to apply stress on the wafer in this situation, a static load applying device (not shown) is activated keeping each of the air pressure cylinders 33-1, 33-2, . . . and 33-6 be activated. With the activation of the static load applying device, the wafer holding portion on the movable side 4b is pulled via the pulling rod 6 so that tensional load is applied to the wafer W held by the wafer holding portions 4a, 4b. As the periphery of the wafer W is pressed to be held between cushion members with activated air pressure cylinders, uniform static tensional stress is applied on the wafer.

Figure 14A:
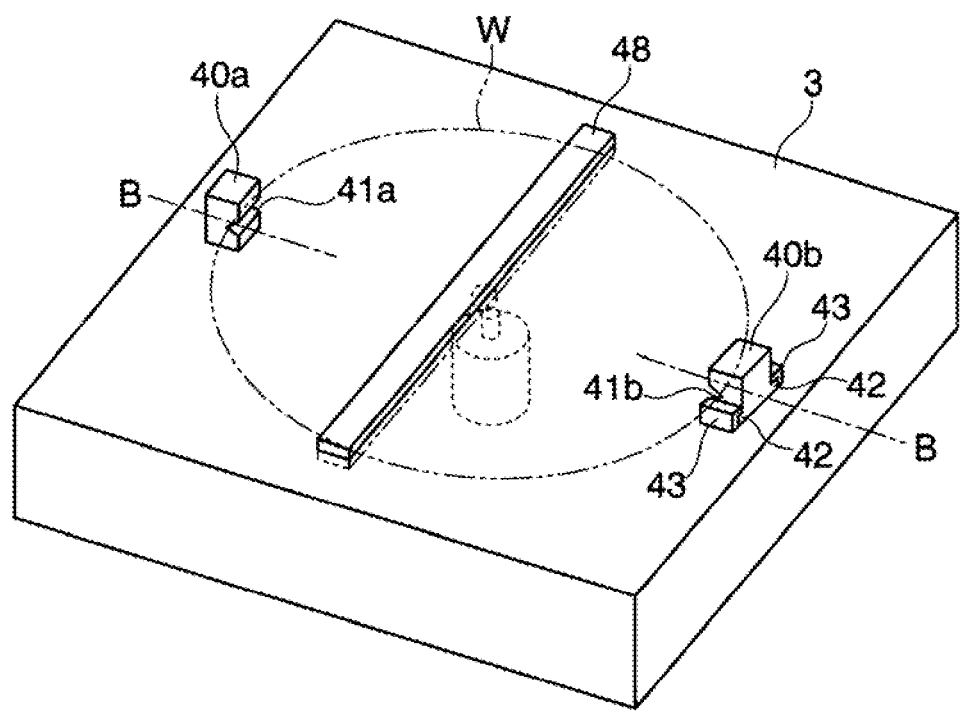
FIG. 14 (*a*) is a perspective view showing the constitution of a static bending load applying portion and (b) is a sectional view along a plane passing through the central line B-B in (a)
Figure 14B:
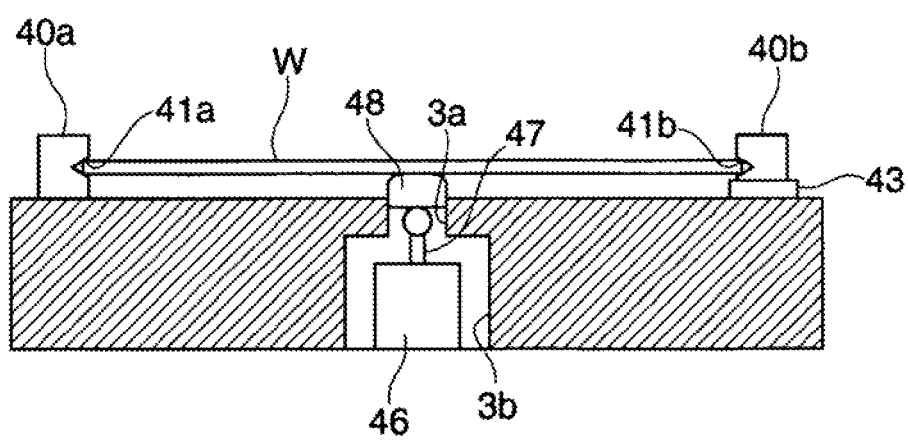

FIG. 14(a) shows in a perspective View an stress applying portion in the arrangement where stress is applied on a wafer through applying static bending load and FIG. 14(b) is a sectional view of FIG. 14(a) in a vertical plane passing through the center line B-B. The defect inspection has a constitution similar to the above mentioned, expect that the stress applying portion is an arrangement by applying static bending load shown in FIG. 14(a),(b) instead of an arrangement by applying static tensional load shown in FIG. 13(a).

The wafer supporting bed 3 is attached integrally to the upper movable portion of the X-Y stage. A longitudinal groove or slit is formed at the center portion on the upper face of the wafer supporting bed and both side faces serve as guide faces 3a of a pressing member 48 disposed in the groove and movable so as to push up the center portion of the wafer W. The lower portions of the guide faces 3a are made to have a narrower space so as to block the downward motion of the pressing member 48 and communicate in its lower portion with an inner space formed at the center position of the wafer supporting bed and contoured by inner faces 3b. In the inner space contoured by inner faces 3b, a load applying device 46 using a piezo-electric (PZT) actuator for applying Z-direction load to push up the wafer potion is disposed and the end portion of a rod member 47 activated by the load applying device 46 is to push up the underside face of the pressing member 48. The upper side face of the pressing member 48 has a smooth curved surface and pushes up the underside face of the placed wafer W.

On the upper face of the wafer supporting bed 3, wafer holding portions 40a, 40b for holding a wafer at its both sides are provided at the positions symmetric in relation to the groove with guide faces 3a enclosing the pressing member 48. The wafer holding portions 40a, 40b are of basically the same and symmetric shape and have V-shaped grooves 41a, 41b formed respectively so as to be confronted each other. One wafer holding portion 40a is fixed on the upper face of the wafer supporting bed 3 and the other wafer holding portion 40b has protruded lower portions 42, 42 which are slidably engaged with the shoes 43, 43 secured on the bed 3.

When a wafer W is to be held in the position shown by imaginary line in FIG. 14(a), the wafer holding portion 40b is kept in retracted position at first. Then one peripheral end of the wafer W is caused to abut on the V-shaped groove 41a, after which the other wafer holding portion 40b is caused to advance so that the other peripheral end of the wafer abut on the V-shaped groove 41b. In this situation, the wafer W is simply supported by the wafer holding portions 40a, 40b in relation to bending action. It is advantageous to hold the wafer W at the determined position in a stable situation by providing a clicking mechanism in which a groove is formed on the underside face of the wafer holding portion 40b and a ball urged upwards by a spring is disposed in the groove on the upper face of the bed 3.

Besides the arrangement where V-shaped grooves are formed preliminarily on the respective wafer holding portions as shown in FIG. 14(a), (b), wafer holding portions for simply supporting the peripheral ends of a wafer may be constituted to be, for example, in an arrangement where each of wafer holding portions 40a, 40b is formed to consist of two parts divided by the horizontal plane passing through the vertex of the V-shaped grooves on the respective wafer holding portions 40a, 40b, the respective lower parts are fixed on the wafer supporting bed 3, the respective upper parts are detachably attached to the lower parts and can be held with anchoring members or the like. In this case, respective upper parts and lower parts are formed in such a manner that respective upper parts and lower parts have configuration of V-shaped grooves similar to those of the wafer holding portions 40a, 40b shown in FIG. 14(*a*), (*b*) in the state where the upper parts are placed on the lower parts and held with anchoring members respectively. Respective upper parts are held in position in the state where peripheral ends of a wafer are placed on the lower parts. In this arrangement, each of lower parts may be fixed to the upper side face of the wafer supporting bed 3.

In the embodiment shown in FIG. 14(*a*),(*b*), when bending load is to be applied to the wafer W in upward direction, the underside face of the wafer W is pushed up via the pressing member 48 by the end of the rod member 47 activated by the load applying device 46 employing an actuator. Instead, another arrangement may be adopted in which the underside face of the wafer W is pushed up directly by the end of the rod member 47 activated by the load applying device 46 without a pressing member intervening. In this case, it is necessary that the end of the rod member 47 has a rather large radius of curvature and the end of the rod member pushes up the underside face of the wafer W at the precise center position.

Figure 15A:
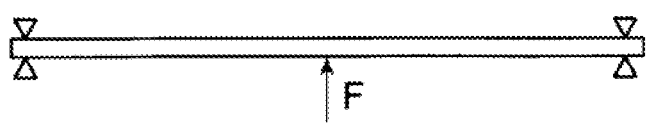
FIG. 15 (*a*) is a schematic view of a wafer considered as a beam subjected to bending action, (b) is a graph showing the bending moment due the static bending load on a wafer and (c) is a graph showing the static bending stress applied to a wafer.
Figure 15B:
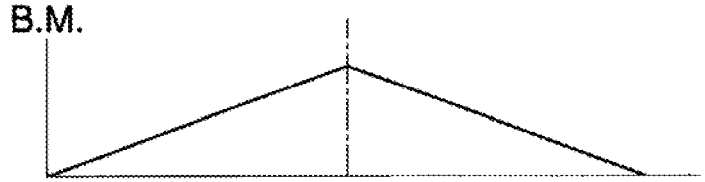
Figure 15C:
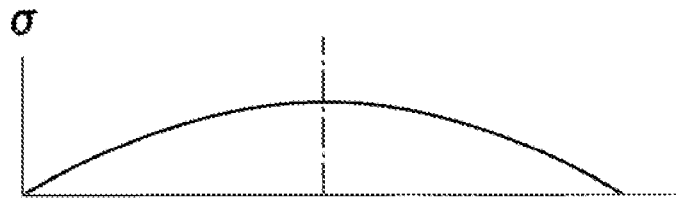

FIG. 15(*a*) to (*c*) is a schematic view for explanation of bending action of a wafer, in which FIG. 15(*a*) is a view showing a wafer supported simply as seen in lateral direction. When load is applied to the wafer in upward direction at its center position, the distribution of bending moment (B.M.) will be as shown in FIG. 15(*b*). When the bending moment is M and the modulus of section is 2, the tensional stress σ in the upper face by the bending becomes M/Z. Considering that the modulus of section of the wafer decreases gradually from the center to an end, the tensional stress occurring in the upper side face of the wafer W with the bending moment distributed as shown in FIG. 15(*b*) becomes as shown in FIG. 15(*c*).

In such a manner, it is possible to apply bending load to a wafer as well as to apply tensional stress to the upper side face of the wafer, as the detected surface on which laser is irradiated, by use of a stress applying device shown in FIG. 14(*a*), (*b*). In a defect inspection apparatus equipped with the stress applying device shown in FIG. 14(*a*), (*b*), the pressing member 48 is in the position with its end near the underside face of the wafer W and stress is not applied to the wafer W at first in the state where the wafer w is held in position with the holding members 40a, 40b on the wafer supporting bed 3. In this state, by activating the load applying device 46 and applying load to the wafer W upwards to create bending action, tensional stress is applied to the wafer in the upper side face and compressing stress is applied to the wafer in the underside face. In defect inspection, it is preferable to make displacement of the wafer in its center portion due to the bending load applied to the wafer be an order of 0.1 to 0.3 mm in case of a 200 mm wafer.

Figure 16:
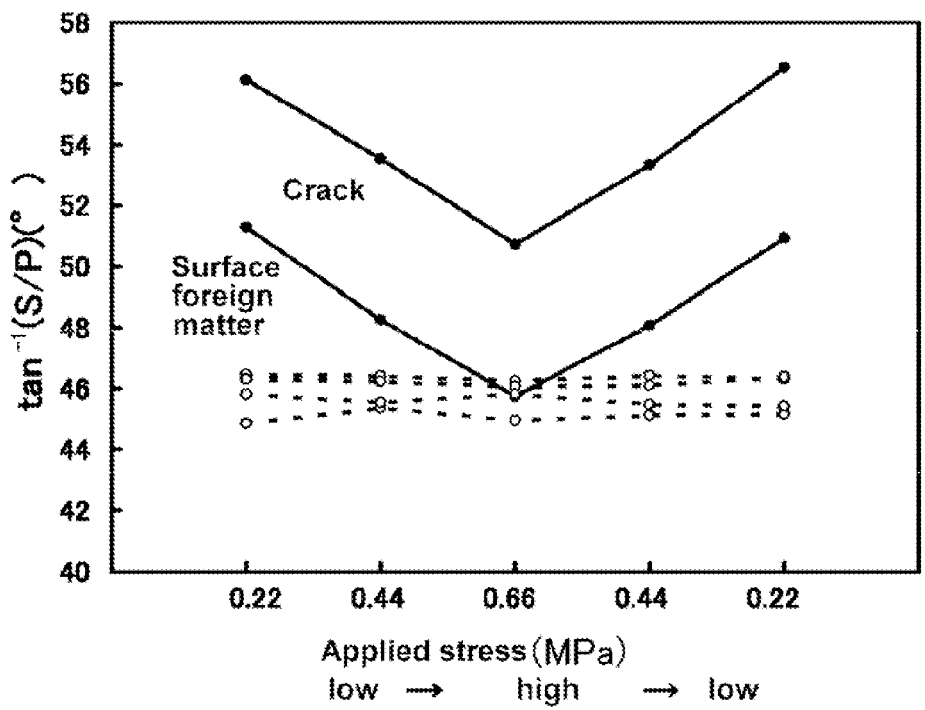
FIG. 16 is a graph showing variation of polarization direction due to defects corresponding to the position on the wafer surface under bending action applied to a wafer.

FIG. 16 shows a result of measurement of variation of polarization direction due to defects corresponding to the position on the wafer surface under bending action applied to a wafer so as to create tensional stress in the upper side face of the wafer. When bending load is applied to the wafer, tensional stress is high in the center of the wafer and low towards peripheral portion as shown in FIG. 15(*c*). In the case of defect being cracks, polarization direction (P/S), which varies corresponding to stress concentration due to application of tensional stress, varies largely corresponding to variation of stress. In the case of defect being surface foreign matter, which does not accompany stress concentration, polarization direction does not vary so much due to variation of stress.

Figure 17:
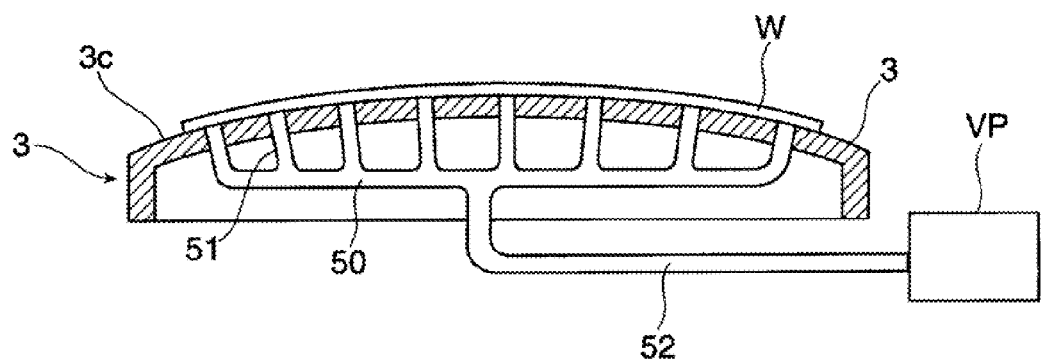
FIG. 17 a view showing partially in section another arrangement of a static bending load applying portion.

FIG. 17 is a schematic view for explaining another arrangement for creating bending action in a wafer as shown in partial section. The wafer supporting bed 3 has an upper side face 3c of a cylindrical shape and plurality of holes for suction are formed thereon. Vacuum suction is made with a vacuum pump VP through each of holes via channels 51, channels 50 and 52. A wafer W is placed on the upper side face 3c of the wafer supporting bed 3 and temporarily held with holding means (not shown), thus giving a state where no stress is applied to the wafer W.

In this state, when stress is to applied to the wafer W, temporary holding of the wafer W with holding means is removed and vacuum suction is made by activation of the vacuum pump VP through holes via channels 51 so as to attract the wafer W onto the upper face 3c of the wafer supporting bed 3. Due to this, the wafer w is deformed to be a shape conforming to the cylindrical shape of the upper face 3c and the wafer W is subjected to bending deformation so as to have a uniform curvature, thus creating uniform tensional stress along the upper side face of the wafer W. While the cylindrical shape is exaggerated in FIG. 17, configuration necessary for actual bending deformation will be of more gentle and subtle curvature. Further, each of holes formed on the upper face 3c of the wafer supporting bed 3 should be worked so as to have smooth surface in order not to cause damage on the wafer when it is attracted and held by suction.

Figure 18:
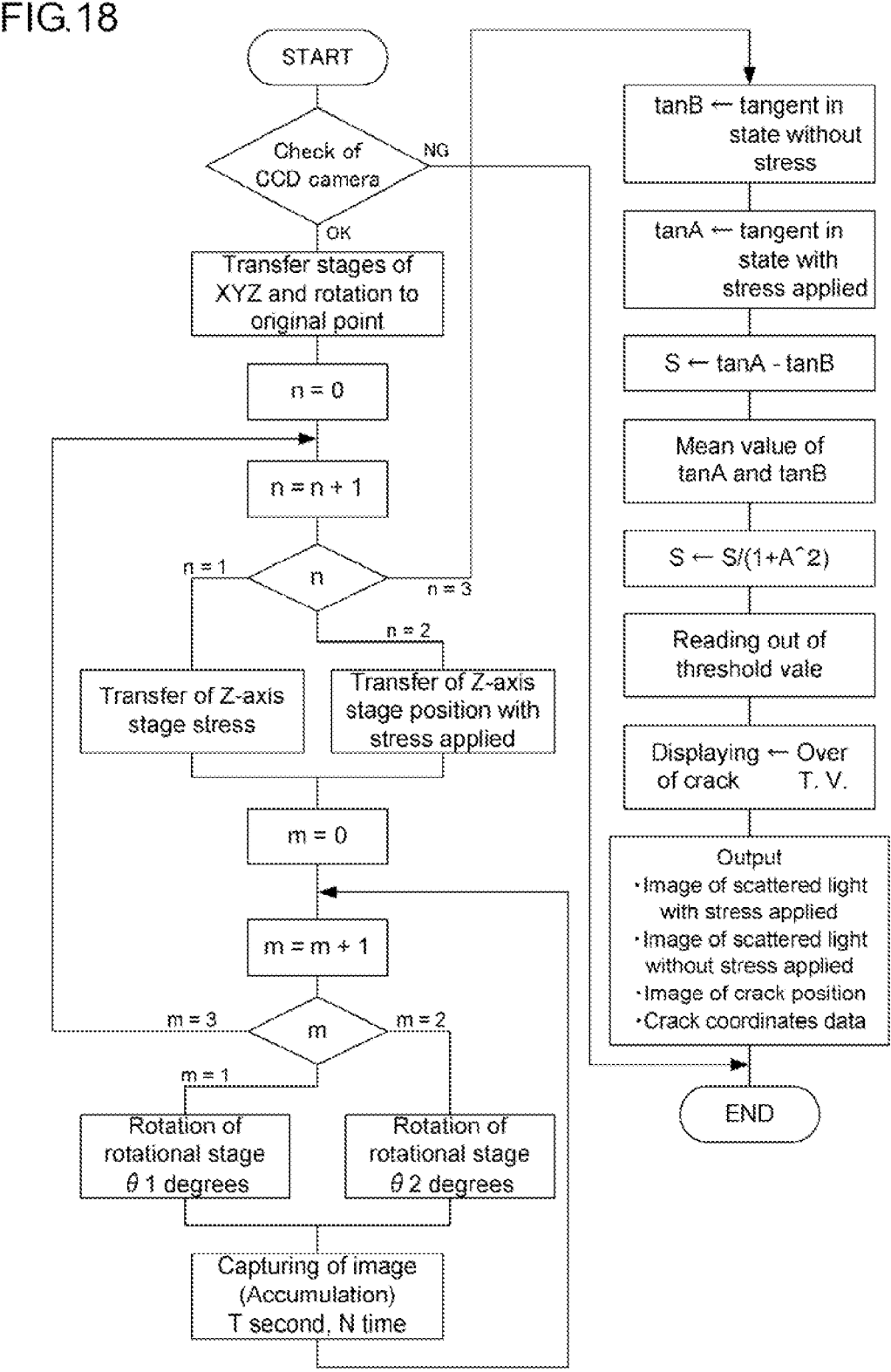
FIG. 18 is a flow chart showing an example of operation in which cracks are detected by use of the defect inspecting apparatus according to the present invention.

FIG. 18 is a flow chart showing an example of operation in which polarized states of scattered light before and after stress is applied to the wafer as an object to be inspected are compared and difference over a threshold value is determined to exhibit a crack by use of the defect inspection apparatus according to the present invention. Defect inspection by use of the defect inspection apparatus is performed through the following steps. The defect inspection apparatus in this example corresponds to defect inspection of a wafer with wiring layers formed and has the analyzer on the light receiving side made rotatable.

(1) Situation of cooled CCD-camera is detected. Detection of NG results in forcible end. If situation of CCD-camera is OK, after each stage of X, Y, Z and analyzer rotation has been returned to original point, X-Y stage is made to advance to the position for image capturing and stop.

(2) Parameter n is such that n=1 means 'stress is not applied' and n=2 means 'stress is applied'. In a state where stress is applied, Z-stage is made to move so as to create displacement in the center of the wafer. Amount of displacement differs depending on the size of the wafer, generally being in a range of hundreds μm (displacement under application of tensional stress of several MPa).

(3) Parameter m designates angle of the analyzer. When m=1 command of angle θ1 is given and when m=2 command of θ2 is given to the rotation stage respectively. In order to decrease scattered light from patterns, it is desired to employ angles θ1, θ2 in approximation to cross-Nicol angle (for example, 90 degrees, 85 degrees, etc. for S-polarized incident light).

(4) Image capturing is performed for T second and N times and captured image data is stored, in order to make SN ratio high in state with or without application of stress and in state of each angle of the analyzer (for example, T=1000 ms, N=50 times).

(θ) The main axis directions (tan θ) of polarization of scattered light before and after application of stress are calculated. Calculation is made for tan B with stress applied and tan B without stress applied.

(6) The variation from tan B to tan A is made be S.

(7) Because tan e is not linear, S is divided by differential of tan θ (1+tan θ^2). For this calculation, mean value of tan A and tab B is calculated and division is made by use of the mean value A.

(8) Threshold value of S is read out, a defect is decided to be a crack when S is over the threshold value at each position in an image.

(9) Images of scattered light are stored for those before and after application of stress and at (four) combinations of analyzer angle. Images explicitly showing positions of cracks are displayed and stored. Output of coordinate values (X, Y) of cracks is made to CSV file.

The situation where the method for inspecting defects and the defect inspecting apparatus according to the present invention is used for actual application will be mentioned.

A wafer as an object to be inspected is held, carried and placed to be held on the determined position in the defect inspecting apparatus. Then, just after confirming the placed position of the wafer, while polarized light is irradiated on the fore side surface of the wafer in state where stress is not applied and scanned through the surface, scattered light is detected and data processing is performed. After the processing sequence has been accomplished, applying stress on the wafer with application of load in upward direction, similar operation of detection of scattered light and data processing are performed. After this, detection of defects and classification thereof are performed in a manner where intensities of P-polarized component and S-polarized component before and after stress is applied, polarization direction as ratio of the intensities are obtained and processing operation including comparison with a threshold value is performed. The whole process from holding of a wafer to processing operation of inspection results can be accomplished in a short time of about 10 minutes.

<C> Quality Control of Wafers and Semiconductor Devices

The method for inspecting defects and defect inspecting apparatus according to the present invention allows defects to be detected and/or classified accurately in a short time. By installing the defect inspecting apparatus for performing in-line operation of defect inspection in manufacturing process of semiconductor devices from wafers and performing quality control in the manufacturing process including defect inspection, troubles in products can be prevented beforehand, throughput in manufacturing semiconductor devices can be raised and productivity can be improved as a whole.

In manufacturing process of semiconductor devices from wafers, flattening is performed through CMP process after a wiring layer and an insulator layer have been formed and the processing sequence of forming a wiring layer and an insulator layer and then flattening are repeated by plural times, thus devices being formed. In flattening process, there is a possibility of defects occurring in a wafer depending on conditions due to mechanical elements such as slurry liquid, polishing pads or the like. The defects can be reduced by making condition of CMP process optimum. Condition in flattening by CMP process includes structure of polishing pads, structure of conditioning pads, load, rotation rate and constituent, density, pH, grain size, etc. of slurry liquid. While the optimum condition in flattening may vary with lapse of time, situation with no defect occurring can be maintained by providing process of performing defect inspection after CMP process and reflecting its result on changing of condition in CMP.

As mentioned, process management in relation to defects in a wafer can be executed in such a way that detection and/or classification of defects through defect inspection is performed for a wafer, data containing number of sites exhibiting characteristics of polarization intensity and polarization direction over threshold values in the wafer surface, polarization intensity and position of polarization are collected and defect distribution in the wafer surface is displayed, beginning from a wafer in the stage of raw material for manufacturing semiconductor devices and extending through a wafer in each stage where a wiring layer and an insulator layer have been formed and flattening has been performed through CMP process. Because intensive scattered light occurs with metallic wiring patterns in the case of a wafer on which wiring layers are formed, it is preferable to adopt a defect inspection apparatus equipped with an analyzer which can be rotatably adjusted being disposed behind the polarized light separating means (beam displacer BD or the like) on the imaging device side receiving scattered light so as to cut off or decrease the intensive scattered light. Further, in the case of a wafer in the stage where a wiring layer is being formed, wiring patterns are exposed on the surface of the wafer to be inspected. Therefore, measurement of number, size, etc, of defect is to be made for defects which can appear in the insulator layer between the upper and lower wiring layers or in the insulator layer part between the wirings in a plane.

Through performing defect inspection in manufacturing process of semiconductor devices, performing detection and/or classification of defects in each stage of processing steps and performing further processing steps for wafers in a state of few defects, the final products of semiconductor devices can be prevented from being non-conforming. It is known that there is a correlation between number (density) of defects or size of defects in a wafer and performance failure of semiconductor devices. Defects of a size crossing the width of wirings in circuit patterns of semiconductor devices can cause breaking of wire and defects crossing an insulator layer between two wirings (in plane view) can cause short-circuit. Especially in the case of defects being cracks, even if initial performance failure as semiconductor devices does not occur, it is considered that possibility in worsening of durability due to lapse of time becomes higher. The wafers and semiconductor devices having been subjected to inspection of defects and quality control according to the present invention are of sufficient durability and high reliability, as confirmed by accelerated test.

Figure 20:
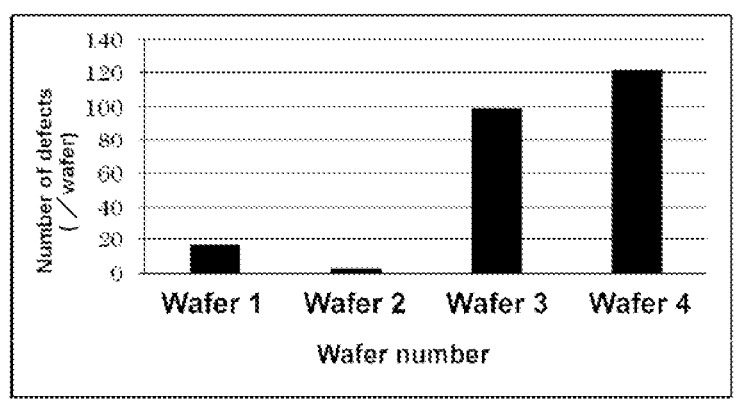
FIG. 20 is a bar graph showing number of defects for wafers shown in FIG. 19 respectively.

FIG. 19 shows captured images of defect distribution on wafers: wafer 1 to 4 having been subjected to CMP procedure for which defect inspection has been performed. The wafer 4, as a result of defect inspection, had many defects such as cracks and its non-conforming rate was high. As a result of defect inspection of the wafer 3, in which condition of CMP was changed, still many defects remained, though defects such as cracks were reduced due to change of condition. As a result of defect inspection of the wafers 1 and 2, in which condition of CMP was further changed, number of defects was reduced to sufficient level. These yielded preferable wafers and semiconductor devices. FIG. 20 is a bar graph showing number of defects per wafer detected in wafers 1, 2, 3 and 4. Let number of chips per wafer be 240, number of defects in the wafer 1 and wafer 2 were 18 and 3 respectively, so the non-conforming rate was considered to be about 7.5% and 1.3% respectively. Number of defects in the wafer 3 and wafer 4 were 127 and 99 respectively with non-conforming rate being 53% and 41 respectively, which was extremely high.

Figure 21:
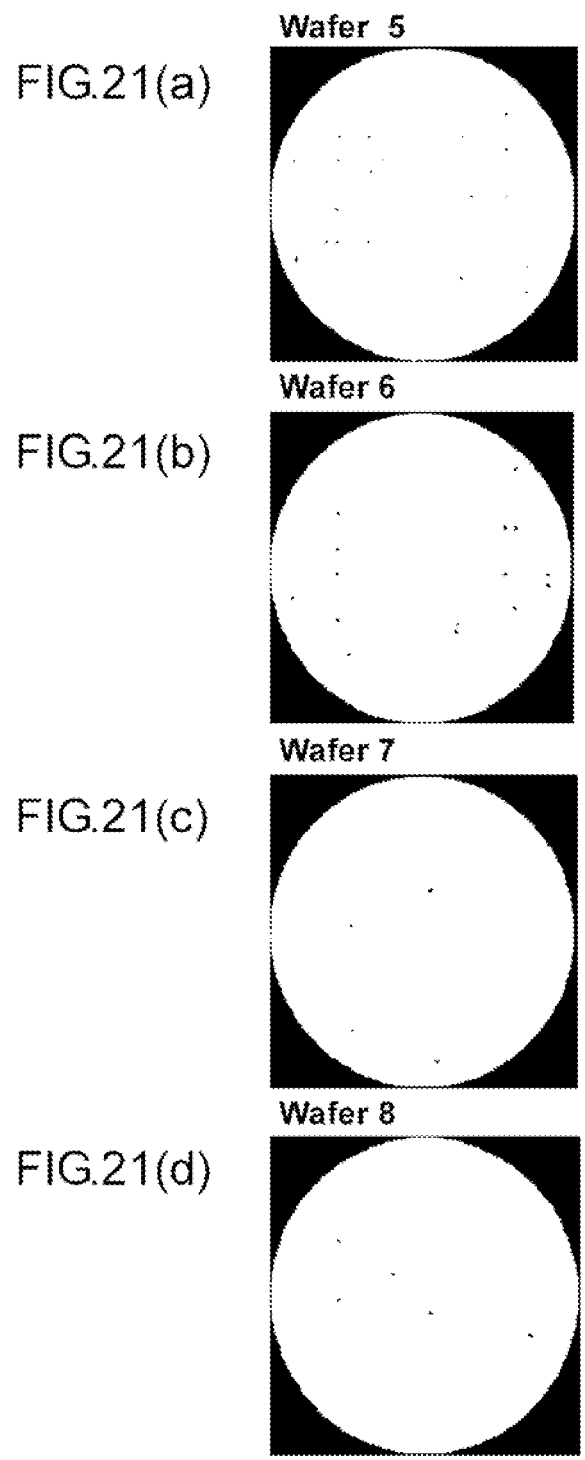
FIG. 21 is captured images of defect distribution on another wafers subjected to CMP procedure for which defect inspection have been actually performed.
Figure 22:
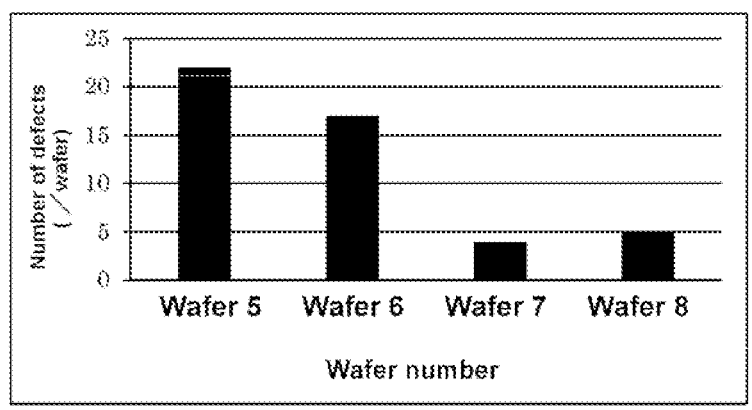
FIG. 22 is a bar graph showing number of defects for wafers shown in FIG. 21 respectively.

Flow of quality control process of wafers will be explained referring to FIG. 21 and FIG. 22. FIG. 21 is captured images of defect distribution on wafer surfaces for (a)wafer 5, (b)wafer 6, (c)wafer 7 and (d)wafer 8. FIG. 22 is a bar graph showing number of defects for wafers shown in FIG. 21 respectively. As a result of defect inspection of the wafer 5 produced at first, number of defects was 22 and non-conforming rate was considered to be about 9.2% when number of chips per wafer was 240. As a result of defect inspection of the wafer 6, prepared with condition of CMP changed, there were still many defects, though reduced to be 17 due to change of condition, and non-conforming rate was about 7%. As a result of defect inspection of the wafers 7, in which condition of CMP was further made optimum, number of defects was 4 and non-conforming rate was estimated to be about 1.7, thus condition of CMP for manufacturing preferable wafers with low non-conforming rate being attained. However, number of defects which were generated in CMP process may vary as time lapses. In this, according to the result where defect inspection was performed for wafer 8 after a certain time lapsed, number of defects was 5 and non-conforming rate was about 2.3%. When defects were generated in a wafer more than in this wafer 8, reliability of such wafer is lowered because of high non-conforming rate. From this, management of processing steps was executed so as to manufacture wafers, in a stable situation, with defects less than in wafer 8. According to the present invention, target value of non-conforming rate in quality control can be established to be low as of 2%.

Further, concerning with such quality control of wafers, necessity for considering the effect of surface roughness which may cause disconnection of wire or short-circuit is comparatively low in the case where one wiring layer alone is formed on a wafer, because another wiring layer is not to be formed on it. However, in the case where two or more wiring layers are formed on a wafer, it is necessary to consider the effect of surface roughness. Therefore, quality control as mentioned above becomes important.

According to the present invention, quality control can be suitably executed for wafers in manufacturing process of semiconductor devices or semiconductor devices manufactured using the wafers and it can be restrained to a great extent for semiconductor devices to result in non-conforming products. On the other hand, the present invention is specified to be a wafer formed through such quality control so as to make number of defects and defect density be less than a determined threshold value and further to be a semiconductor device manufactured using such a wafer so as to decrease extremely possibility giving a non-conforming product.

As disclosed in Non-patent Document 1, it is known that a yield of wafers or semiconductor devices is abruptly lowered when defect density goes over a certain threshold value. It will contribute to improving yield to a great extent to set up a standard value of yield allowable for a mass production factory as a threshold value as renewed, based on the above threshold value, and to select wafers or semiconductor devices in such a manner that they are adapted for the condition as a result of defect inspection.

The present invention can be adapted for quality evaluation of objects to be inspected or determination of how to remove defects, by detecting defects and/or classifying kinds of defects in an object to be inspected, which is made of material with high degree of homogeneity, such as a wafer for manufacturing semiconductor devices, a substrate for manufacturing optical functional devices such as diffraction gratings, a super-lattice construction, a MEMS construction, a glass plate for liquid crystal device panel or reticle. Further, employment of this defect inspection in inspection steps through in-line process may contribute to improvement of product quality or productivity.

What is claimed is:

1. A method for inspecting defects in an object to be inspected by polarizing, with a polarizer, light of a wavelength that can penetrate into the object to be inspected and directing the polarized light onto a surface of the object to be inspected for irradiation thereof, thereby detecting light scattered by the object to be inspected in a state where static stress is not applied to the object to be inspected and in a state where static stress is applied thereto, said method comprising:

directing the polarized light obliquely for irradiation onto the surface of the object to be inspected in a state where static stress is not applied to the object to be inspected and separating scattered light generated as a result of the irradiation into P-polarized component light and S-polarized component light, then obtaining intensity of each component light and polarization direction as a ratio thereof, directing the polarized light obliquely for irradiation onto the surface of the object to be inspected, in a state where static stress is applied to the object to be inspected, at the same position of the surface as when the light was directed for irradiation in a state where no static stress is applied to the object to be inspected and separating scattered light generated as a result of the irradiation into P-polarized component light and S-polarized component light, then obtaining intensity of each component light and polarization direction as a ratio thereof, and detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value;

wherein application of static stress to the object to be inspected is made through fixedly holding the object to be inspected at a part on one end in the periphery thereof, grasping the object to be inspected at the part on the other end in the periphery of thereof and pulling it to apply static tensional load to the object to be inspected, so that application of static stress to the object to be inspected is made so as to generate tensional stress in the object to be inspected as a whole.

2. A method for inspecting defects in an object to be inspected by polarizing, with a polarizer, light of a wavelength that can penetrate into the object to be inspected and directing the polarized light onto a surface of the object to be inspected for irradiation thereof, thereby detecting light scattered by the object to be inspected in a state where static stress is not applied to the object to be inspected and in a state where static stress is applied thereto, said method comprising:

directing the polarized light obliquely for irradiation onto the surface of the object to be inspected in a state where static stress is not applied to the object to be inspected and separating scattered light generated as a result of the irradiation into P-polarized component light and S-polarized component light, then obtaining intensity of each component light and polarization direction as a ratio thereof, directing the polarized light obliquely for irradiation onto the surface of the object to be inspected, in a state where static stress is applied to the object to be inspected, at the same position of the surface as when the light was directed for irradiation in a state where no static stress is applied to the object to be inspected and separating scattered light generated as a result of the irradiation into P-polarized component light and S-polarized component light, then obtaining intensity of each component light and polarization direction as a ratio thereof, and detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value;

wherein application of static stress to the object to be inspected is made through holding the object to be inspected at both ends so as to simply supporting the object to be inspected and pressing the object to be inspected at its center position upwards to apply upward static load generating static bending load on the object to be inspected, so that application of static stress to the object to be inspected is made so as to generate tensional stress on the side of the object to be inspected on which polarized light is directed for irradiation.

3. A method for inspecting defects in an object to be inspected by polarizing, with a polarizer, light of a wavelength that can penetrate into the object to be inspected and directing the polarized light onto a surface of the object to be inspected for irradiation thereof, thereby detecting light scattered by the object to be inspected in a state where static stress is not applied to the object to be inspected and in a state where static stress is applied thereto, said method comprising:

directing the polarized light obliquely for irradiation onto the surface of the object to be inspected in a state where static stress is not applied to the object to be inspected and separating scattered light generated as a result of the irradiation into P-polarized component light and S-polarized component light, then obtaining intensity of each component light and polarization direction as a ratio thereof, directing the polarized light obliquely for irradiation onto the surface of the object to be inspected, in a state where static stress is applied to the object to be inspected, at the same position of the surface as when the light was directed for irradiation in a state where no static stress is applied to the object to be inspected and separating scattered light generated as a result of the irradiation into P-polarized component light and S-polarized component light, then obtaining intensity of each component light and polarization direction as a ratio thereof, and detecting defects and/or classifying the defects by comparing the intensity and polarization direction of each component light obtained in a state where no stress is applied to the object to be inspected and the intensity and polarization direction of each component light obtained in a state where stress is applied to the object to be inspected respectively with a predetermined threshold value;

wherein application of static stress to the object to be inspected is made through placing the object to be inspected on a cylindrically shaped bed with plurality of holes connected to a vacuum suction means formed thereon and performing vacuum suction of the object to be inspected by the vacuum suction means to attract the object to be inspected to the surface of the bed thereby causing bending deformation of the object to be inspected, so that application of static stress on the object to be inspected is made so as to generate tensional stress on the side of the object to be inspected on which polarized light is directed for irradiation.

4. The method for inspecting defects according to any of claims 1 to 3, wherein, in respect of light separated with the polarizer into P-polarized and S-polarized components, intensity of scattered light other than by defects is lowered through rotational adjustment of an analyzer which is interposed on the optical axis so as to be adjustable rotationally around the optical axis.

5. The method for inspecting defects according to claim 1, wherein, in respect of light separated with the polarizer into P-polarized and S-polarized components, intensity of scattered light other than by defects is lowered through rotational adjustment of an analyzer which is interposed on the optical axis so as to be adjustable rotationally around the optical axis.

6. The method for inspecting defects according to claim 2, wherein, in respect of light separated with the polarizer into P-polarized and S-polarized components, intensity of scattered light other than by defects is lowered through rotational adjustment of an analyzer which is interposed on the optical axis so as to be adjustable rotationally around the optical axis.

7. The method for inspecting defects according to claim 3, wherein, in respect of light separated with the polarizer into P-polarized and S-polarized components, intensity of scattered light other than by defects is lowered through rotational adjustment of an analyzer which is interposed on the optical axis so as to be adjustable rotationally around the optical axis.

8. A wafer on which two or more wiring layers have been formed during manufacturing process of semiconductor devices including CMP process and for which inspection has been executed in respect of defects capable of occurrence during CMP process;

wherein said defect inspection is performed in a method for inspecting defects in the wafer by polarizing, with a polarizer, light of a wavelength that can penetrate into the wafer and directing the polarized light onto a surface of the wafer for irradiation thereof, thereby detecting light scattered by the wafer in a state where static stress is not applied to the wafer and in a state where static stress is applied thereto, said method for inspecting defects comprising:

directing the polarized light obliquely for irradiation onto the surface of the wafer in a state where static stress is not applied to the wafer and separating scattered light generated as a result of the irradiation into P-polarized component light and S-polarized component light, then obtaining intensity of each component light and a polarization direction as a ratio thereof, directing the polarized light obliquely for irradiation onto the surface of the wafer, in a state where static stress is applied to the wafer, at the same position of the surface as when the light was directed for irradiation in a state where no static stress is applied to the wafer and separating scattered light generated as a result of the irradiation into P-polarized component light and S-polarized component light, then obtaining intensity of each component light and a polarization direction as a ratio thereof, and detecting defects and/or classifying the defects by comparing the intensity and polarization direction of each component light obtained in a state where no stress is applied to the wafer and the intensity and polarization direction of each component light obtained in a state where stress is applied to the wafer respectively with a predetermined threshold value;

wherein said application of static stress to the object to be inspected is made so as to generate tensional stress on the side of the object to be inspected on which polarized light is directed for irradiation or generate tensional stress in the object to be inspected as a whole, and wherein management of defects in the wafer is executed through obtaining the number and/or size of the defects in said method for inspecting defects, collecting data including number of sites exhibiting characteristics of polarized light intensity and polarization direction over a threshold value in the wafer surface, intensity of polarized light and position of polarized light and displaying distribution of defects in the wafer surface and further management of the wafer is executed so that ratio of non-conforming semiconductor devices manufactured from the wafer having potential cause of insufficiency in conduction or in withstand voltage as a result of defects be lower than a management value defined for each semiconductor device.

9. A semiconductor device manufactured using the wafer according to claim 8 for which defect inspection has been executed.

10. The semiconductor device according to claim 9, wherein said wafer is obtained under management of quality control in which the number and/or size of defects capable of occurrence in an insulator layer between upper and lower wiring layers and/or in an insulator layer between wirings in the layer plane are measured.

11. The wafer according to claim 8 for which defect inspection has been executed, wherein said wafer is obtained under management of quality control in which the number and/or size of defects capable of occurrence in an insulator layer between upper and lower wiring layers and/or in an insulator layer between wirings in the layer plane are measured.

12. A method for quality control of a wafer, on which two or more wiring layers have been formed during manufacturing process of semiconductor devices including CMP process and for which inspection has been executed in respect of defects capable of occurrence during CMP process, or a semiconductor device manufactured using the wafer;

wherein said defect inspection is performed in a method for inspecting defects in the wafer by polarizing, with a polarizer, light of a wavelength that can penetrate into the wafer and directing the polarized light onto a surface of the wafer for irradiation thereof, thereby detecting light scattered by the wafer in a state where static stress is not applied to the wafer and in a state where static stress is applied thereto, said method for inspecting defects comprising:

directing the polarized light obliquely for irradiation onto the surface of the wafer in a state where static stress is not applied to the wafer and separating scattered light generated as a result of the irradiation into P-polarized component light and S-polarized component light, then obtaining intensity of each component light and a polarization direction as a ratio thereof, directing the polarized light obliquely for irradiation onto the surface of the wafer in a state where static stress is applied to the wafer, at the same position of the surface as when the light was directed for irradiation in a state where no static stress is applied to the wafer and separating scattered light generated as a result of the irradiation into P-polarized component light and S-polarized component light, then obtaining intensity of each component light and a polarization direction as a ratio thereof, and detecting defects and/or classifying the defects by comparing the intensity and polarization direction of each component light obtained in a state where no stress is applied to the wafer and the intensity and polarization direction of each component light obtained in a state where stress is applied to the wafer respectively with a predetermined threshold value;

wherein said application of static stress on the wafer is made so as to generate tensional stress on the side of the wafer on which polarized light is directed for irradiation or generate tensional stress in the wafer as a whole, and wherein management of defects in the wafer or semiconductor device is executed through obtaining the number and/or size of the defects in said method for inspecting defects, collecting data including number of sites exhibiting characteristics of polarized light intensity and polarization direction over a threshold value in the wafer surface, intensity of polarized light and position of polarized light and displaying distribution of defects in the wafer surface and further management of the wafer or the semiconductor device is executed so that ratio of non-conforming semiconductor devices manufactured from the wafer having potential cause of insufficiency in conduction or in withstand voltage as a result of defects be lower than a management value defined for each semiconductor device.

13. The method for quality control of a wafer or a semiconductor device according to claim 12, wherein management of quality control has been executed for the wafer or semiconductor device so that the number and/or size of defects capable of occurrence in an insulator layer between upper and lower wiring layers and/or in an insulator layer between wirings in the layer plane be measured.

14. A defect inspecting apparatus, comprising:

a support portion on which an object to be inspected is placed, static stress applying means capable of switching between a state where static stress is applied to the object to be inspected placed on the support portion and a state where no static stress is applied to the object to be inspected, a light source device that emits light with a wavelength that can penetrate into the object to be inspected via a polarizer obliquely onto a surface of the object to be inspected supported by the support portion, a scanning driving unit that cause the object to be inspected and the light source device to move relatively to each other, means for separating polarized light into P-polarized component light and S-polarized component light disposed at a position in a dark field for receiving scattered light of the light directed onto the object to be inspected for irradiation thereof, light-receiving means having a P-polarized light-receiving section and a S-polarized light-receiving section that separately detect P-polarized component light and S-polarized component light separated by the means for separating polarized light into P-polarized component light and S-polarized component light, a control unit that controls an operation including a static stress application state by the static stress applying means and relative motion of the light source device and the object to be inspected by the scanning driving unit, and a processing unit that detects defects and/or determines types of defects in the object to be inspected by comparing the intensities of P-polarized component light and S-polarized component light as detected by the light-receiving means and a polarization direction thereof obtained as a ratio of the intensities in a state where static stress is applied to the object to be inspected and in a state where no static stress is applied to the object to be inspected respectively with a predetermined threshold value;

wherein said support portion of the object to be inspected is equipped with a holding portion on the fixed side holding a part of the periphery of the object to be inspected and a holding portion on the movable side holding another part of the periphery of the object to be inspected, wherein said static stress applying means applies static tensional load on the object to be inspected by pulling the holding portion on the movable side, and wherein said static stress applying means is arranged so as to apply static tensional load to the object to be inspected to generate static tensional stress in the object to be inspected as a whole.

15. A defect inspecting apparatus, comprising:

a support portion on which an object to be inspected is placed, static stress applying means capable of switching between a state where static stress is applied to the object to be inspected placed on the support portion and a state where no static stress is applied to the object to be inspected, a light source device that emits light with a wavelength that can penetrate into the object to be inspected via a polarizer obliquely onto a surface of the object to be inspected supported by the support portion, a scanning driving unit that cause the object to be inspected and the light source device to move relatively to each other, means for separating polarized light into P-polarized component light and S-polarized component light disposed at a position in a dark field for receiving scattered light of the light directed onto the object to be inspected for irradiation thereof, light-receiving means having a P-polarized light-receiving section and a S-polarized light-receiving section that separately detect P-polarized component light and S-polarized component light separated by the means for separating polarized light into P-polarized component light and S-polarized component light, a control unit that controls an operation including a static stress application state by the static stress applying means and relative motion of the light source device and the object to be inspected by the scanning driving unit, and a processing unit that detects defects and/or determines types of defects in the object to be inspected by comparing the intensities of P-polarized component light and S-polarized component light as detected by the light-receiving means and a polarization direction thereof obtained as a ratio of the intensities in a state where static stress is applied to the object to be inspected and in a state where no static stress is applied to the object to be inspected respectively with a predetermined threshold value;

wherein said support portion of the object to be inspected is equipped with a pair of holding portions which simply support the object to be inspected at both opposing peripheral ends, wherein said static stress applying means is equipped with a pressing member for pushing up the object to be inspected at the center position between the opposing ends thereof and static load applying means for applying static bending load to the object to be inspected by pushing up the pressing member to apply upward static load on the object to be inspected, and wherein said static stress applying means is arranged so as to apply static bending load to the object to be inspected to generate static tensional stress on the side of the object to be inspected on which polarized light is directed for irradiation.

16. A defect inspecting apparatus, comprising:

a support portion on which an object to be inspected is placed, static stress applying means capable of switching between a state where static stress is applied to the object to be inspected placed on the support portion and a state where no static stress is applied to the object to be inspected, a light source device that emits light with a wavelength that can penetrate into the object to be inspected via a polarizer obliquely onto a surface of the object to be inspected supported by the support portion, a scanning driving unit that cause the object to be inspected and the light source device to move relatively to each other, means for separating polarized light into P-polarized component light and S-polarized component light disposed at a position in a dark field for receiving scattered light of the light directed onto the object to be inspected for irradiation thereof, light-receiving means having a P-polarized light-receiving section and a S-polarized light-receiving section that separately detect P-polarized component light and S-polarized component light separated by the means for separating polarized light into P-polarized component light and S-polarized component light, a control unit that controls an operation including a static stress application state by the static stress applying means and relative motion of the light source device and the object to be inspected by the scanning driving unit, and a processing unit that detects defects and/or determines types of defects in the object to be inspected by comparing the intensities of P-polarized component light and S-polarized component light as detected by the light-receiving means and a polarization direction thereof obtained as a ratio of the intensities in a state where static stress is applied to the object to be inspected and in a state where no static stress is applied to the object to be inspected respectively with a predetermined threshold value;

wherein said support portion of the object to be inspected is formed to be a cylindrically shaped bed on which plurality of suction holes are formed so as to communicate with a vacuum suction means via piping and the object to be inspected is deformed by activation of the vacuum suction means so that the object to be inspected be attracted towards the surface of the cylindrically shaped bed and deformed with bending action, and wherein said static stress applying means is arranged so as to apply static bending load to the object to be inspected to generate static tensional stress on the side of the object to be inspected on which polarized light is directed for irradiation.

17. The defect inspecting apparatus according to any of claims 14 to 16,
wherein a polarizer plate as an analyzer is disposed between the means for separating polarized light and the light-receiving means and the polarizer plate as an analyzer is rotationally adjustable around the optical axis.

18. The defect inspecting apparatus according to claim 14, wherein a polarizer plate as an analyzer is disposed between the means for separating polarized light and the light-receiving means and the polarizer plate as an analyzer is rotationally adjustable around the optical axis.

19. The defect inspecting apparatus according to claim 15, wherein a polarizer plate as an analyzer is disposed between the means for separating polarized light and the light-receiving means and the polarizer plate as an analyzer is rotationally adjustable around the optical axis.

20. The defect inspecting apparatus according to claim 16, wherein a polarizer plate as an analyzer is disposed between the means for separating polarized light and the light-receiving means and the polarizer plate as an analyzer is rotationally adjustable around the optical axis.

\* \* \* \* \*